(12) United States Patent
Appendino et al.

(10) Patent No.: US 9,701,618 B2
(45) Date of Patent: Jul. 11, 2017

(54) CANNABIDIOL QUINONE DERIVATIVES

(71) Applicant: VIVACELL BIOTECHNOLOGY ESPAÑA S.L., Córdoba (ES)

(72) Inventors: Giovanni Appendino, Turin (IT); María Luz Bellido Cabello De Alba, Córdoba (ES); Eduardo Muñoz Blanco, Córdoba (ES)

( * ) Notice: Subject to any disclaimer, the term of this patent is extended or adjusted under 35 U.S.C. 154(b) by 0 days.

(21) Appl. No.: 15/304,810

(22) PCT Filed: Apr. 16, 2014

(86) PCT No.: PCT/EP2014/057767
§ 371 (c)(1),
(2) Date: Oct. 17, 2016

(87) PCT Pub. No.: WO2015/158381
PCT Pub. Date: Oct. 22, 2015

(65) Prior Publication Data
US 2017/0044092 A1 Feb. 16, 2017

(51) Int. Cl.
C07C 225/28 (2006.01)
C07C 69/95 (2006.01)

(52) U.S. Cl.
CPC ............ *C07C 225/28* (2013.01); *C07C 69/95* (2013.01); *C07B 2200/07* (2013.01); *C07C 2601/16* (2017.05); *C07C 2602/42* (2017.05)

(58) Field of Classification Search
None
See application file for complete search history.

(56) References Cited

U.S. PATENT DOCUMENTS 8,772,349 B2 * 7/2014 Munoz Blanco ....... C07C 50/28
514/690

FOREIGN PATENT DOCUMENTS

EP 2551255 A1 1/2013
WO 2011117429 A1 9/2011

OTHER PUBLICATIONS

Ahmadian, M.; Suh, J.M.; Hah, N.; Liddle, C.; Atkins, A.R.; Downes, M.; Evans, R.M.; "PPARγ signaling and metabolism: the good, the bad and the future", Nat Med., (2013), vol. 19, pp. 557-566.
Barish GD; Narkar VA; Evans RM, "PPARδ: a dagger in the heart of the metabolic syndrome", J Clin Invest., (2006), vol. 116, pp. 590-597.
Bernardo A; Minghetti L, "Regulation of Glial Cell Functions by PPAR—gamma natural and Synthetic Agonists", PPAR Res., (2008), p. 864140.
Bolton JL; Trush MA; Penning TM; Dryhurst G; Monks TJ, "Role of quinones in toxicology", Chem Res Toxicol., (2000), vol. 3, pp. 135-160.
Burstein S, "PPAR-gamma: a nuclear receptor with affinity for cannabinoids", Life Sci, (2005), vol. 77, pp. 1674-1684.
Ciudin A; Hernandez C; SIM6 R, "Update on cardiovascular safety of PPARgamma agonists and relevance to medicinal chemistry and clinical pharmacology", Curr Top Med Chem., (2012), vol. 12, pp. 585-604.
Doshi LS; Brahma MK; Bahirat UA; Dixit AV; Nemmani KV, "Discovery and development of selective PPAR gamma modulators as safe and effective antidiabetic agents", Expert Opin Investig Drugs, (2012), vol. 19, pp. 489-512.
Ferguson H.E.; Kulkarni A.; Lehmann G.M.; Garcia-Bates T.M.; Thatcher T.H.; Huxlin K.R. et al; "Electrophilic peroxisome proliferator-activated receptor-gamma ligands have potent antifibrotic effects in human lung fibroblasts", Am J Respir Cell Mol Biol., (2009), vol. 41, pp. 722-730.
Fievet C; Fruchart J.C.; Staels B.; "PPAR alpha and PPAR gamma dual agonists for the treatment oftype2 diabetes and the metabolicsyndrome", Curr. Opin. Pharmacol., (2006), vol. 6, pp. 606-614.
Gelman, L.; Feige, J.N.; Desvergne, B., "Molecular basis of selective PPARgamma modulation for the treatment of type 2 diabetes", Biochim. Biophys.Acta, (2007), vol. 1771, No. 8, pp. 1094-1107.
Ghoochani A; Shabani K; Peymani M; Ghaedi K; Karamali F; Karbalaei K; Tanhaie S; Salamian A; Esmaeili A; Valian-Borujeni S, "The influence of peroxisome proliferator-activated receptor g(1) during differentiation of mouse embryonic stem cells to neural cells", Differentiation, (2012), vol. 83, pp. 60-67.
Granja AG; Carrillo-Salinas F; Pagani A; Gomez-Canas M; Negri R; Navarrete C; Mecha M; MESTRE L; Fiebich BL; Cantarero I, "A cannabigerol quinone alleviates neuroinflammation in a chronic model of multiple sclerosis", J Neuroimmune Pharmacol., (2012), vol. 4, pp. 1002-1016.

(Continued)

Primary Examiner — Brian J Davis
(74) Attorney, Agent, or Firm — Moore Patents; David Dreyfuss

(57) ABSTRACT

The present invention relates to novel cannabidiol quinone derivatives of formula (I) (I) wherein R is the carbon atom of a, linear or branched group, represented by: alkyl, aryl, alkenyl, alkynyl, acyl or alkoxycarbonyl groups; or wherein R is the nitrogen atom of a, linear or branched group represented by: alkylamine, arylamine, alkenylamine or alkynylamine groups. The invention also relates to the use of any of the compounds of formula (I) as medicaments in therapy, particularly for treating diseases and conditions responsive to PPARg modulation due to their high PPARg agonistic effect lacking electrophilic (Nrf2 activation) and cytotoxic activities. This invention also provides pharmaceutical compositions comprising said compounds and method of treating diseases with said compounds.

(I)

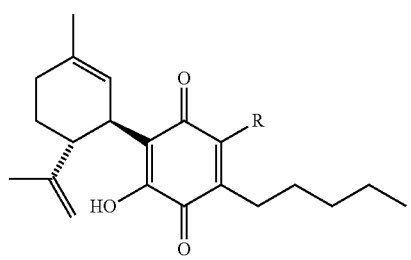

7 Claims, 13 Drawing Sheets

(56) References Cited

OTHER PUBLICATIONS

Itoh T; Fairall L; Amin K; Inaba Y; Szanto A; Balint BL; Nagy L; Yamamoto K; Schwabe JW, "Structural basis for the activation of PPARgamma by oxidized fatty acids", Nat Struct Mol Biol, (2008), vol. 15, pp. 924-931.

Kogan NM; Rabinowitz R; Levi P; Gibson D; Sandor P; Schlesinger M; Mechoulam R, "Synthesis and antitumor activity of quinonoid derivatives of cannabinoids", J Med Chem, (2004), vol. 47, pp. 3800-3806.

Lehmann JM; Moore LB; Smith-Oliver TA; Wilkison WO; Willson TM; Kliewer SA, "An antidiabetic thiazolidinedione is a high affinity ligand for peroxisome proliferator-activated receptor gamma (PPAR gamma", J Biol Chem., (1995), vol. 270, pp. 12953-12956.

Li Y; Zhang J; Schopfer FJ; Martynowski D; Garcia-Barrio MT; Kovach A; Suino-Powell K; Baker PR; Freeman BA; Chen YE, "Molecular recognition of nitrated fatty acids by PPAR gamma", Nat Struct Mol Biol, (2008), vol. 15, pp. 865-867.

Liberato MV; Nascimento AS; Ayers SD; Lin JZ; Cvoro A; Silveira RL; Martinez L; Souza PC; Baidemberg D; Deng T, "Medium Chain Fatty Acids Are Selective Peroxisome Proliferator activated Receptor (PPAR) c Activators and Pan-PPAR Partial Agonists", PLOS ONE, (2012), vol. 7, p. E36297.

Liu J; Li H; Burstein SH; Zurier RB; Chen JD, "Activation and binding of peroxisome proliferator-activated receptor gamma by synthetic cannabinoid ajulemic acid", Mol. Pharmacol., (2003), vol. 63, pp. 983-992.

Monks TJ; Jones DC, "The metabolism and toxicity of quinones, quinonimines, quinone methides, and quinone-thioethers", Curr Drug Metab., (2002), vol. 4, pp. 425-438.

Morales P; Vara D; Gomez-Canas M; Zuniga MC; Olea-Azar C; Goya P; Fernandez-Ruiz J; Diaz-Laviada I; Jagerovic N, "Synthetic cannabinoid quinones: preparation, in vitro antiproliferative effects and in vivo prostate antitumor activity", Eur J Med Chem., (2013), vol. 70, pp. 111-119.

Na HK; Surh YJ, "Oncogenic potential of Nrt2 and its principal target protein heme oxygenase-1", Free Radic Biol Med., (2013), vol. 67, pp. 353-365.

Nolte RT; Wisely GB; Westin S; Cobb JE; Lambert MH; Kurokawa R; Rosenfeld MG; Willson TM; Glass CK; Milburn MV, "Ligand binding and co-activator assembly of the peroxisome proliferator-activated receptor-gamma", Nature, (1998), vol. 395, pp. 137-143.

O'Sullivan Se, "Cannabinoids go nuclear: evidence for activation of peroxisome proliferator-activated receptors", BR J Pharmacol., (2007), vol. 152, pp. 576-582.

Poulsen L; Siersbaek M; Mandrup S, "PPARs: fatty acid sensors controlling metabolism", Semin Cell Dev Biol., (2012), vol. 23, pp. 631-639.

Rosen ED; Macdougald OA, "Adipocyte differentiation from the inside out", Nat Rev Mol Cell Biol., (2006), vol. 7, pp. 885-896.

Solis L. M.; Behrens C.; Dong W.; Suraokar M.; Ozburn N. C.; Moran C. A.; Corvalan A. H.; Biswal S.; Swisher S. G.; Bekele B. N.; "Nrf2 and Keap1 abnormalities in non-small cell lung carcinoma and association with clinicopathologic features", Clin Cancer Res., (2010), vol. 16, pp. 3743-3753.

Sporn, M. B.; Liby, K. T.; "NRF2 and cancer: the good, the bad and the importance of context", Nat. Rev. Cancer, (2012), vol. 12, pp. 564-57.

Stienstra R; Duval C; Muller M; Kersten S, "PPARs, obesity, and inflammation", PPAR Res., (2007), p. 95974.

Sun Y; Bennett A, "Cannabinoids: A New Group of Agonists of PPARs", PPAR Res., (2007), p. 23513.

Széles, L; Torocsik, D.; Nagy, L., "PPARgamma in immunity and inflammation: cell types and diseases", Biochim. Biophys. Acta, (2007), vol. 1771, pp. 1014-1030.

Tachibana K; Yamasaki D; Ishimoto K; Doi T, "The Role of PPARs in Cancer", PPAR Res., (2008), p. 102737.

Tontonoz P; Spiegelman BM, "Fat and beyond: the diverse biology of PPARgamma", Annu Rev Biochem., (2008), vol. 77, pp. 289-312.

Vanden Berghe W; Vermeulen L; Delerive P; Debosscher K; Staels B; Haegeman G, "A paradigm for gene regulation: inflammation, NF-kB and PPAR", Adv.Exp.Med.Biol., (2003), vol. 544, pp. 181-196.

Wang W; Liu F; Chen N, "Peroxisome proliferator-activated receptor-gamma (PPAR-gamma) agonists attenuate the profibrotic response induced by TGF-betal in renal interstitial fibroblasts", Mediators Inflamm, (2007), p. 62641.

Zhao C; Chen W; Yang L; Chen L; Stimpson SA; Diehl AM, "PPARgamma agonists prevent TGFbetal/Smad3-signaling in human hepatic stellate cells", Biochem Biophys Res Commun., (2006), vol. 350, pp. 385-391.

Zhang GY; Yi CG; Li X; Ma B; Li ZJ; Chen XL; Guo SZ; Gao WY, "Troglitazone suppresses transforming growth factor-betal-induced collagen type I expression in keloid fibroblasts", BR J Dermatol., (2009), vol. 160, pp. 762-770.

* cited by examiner

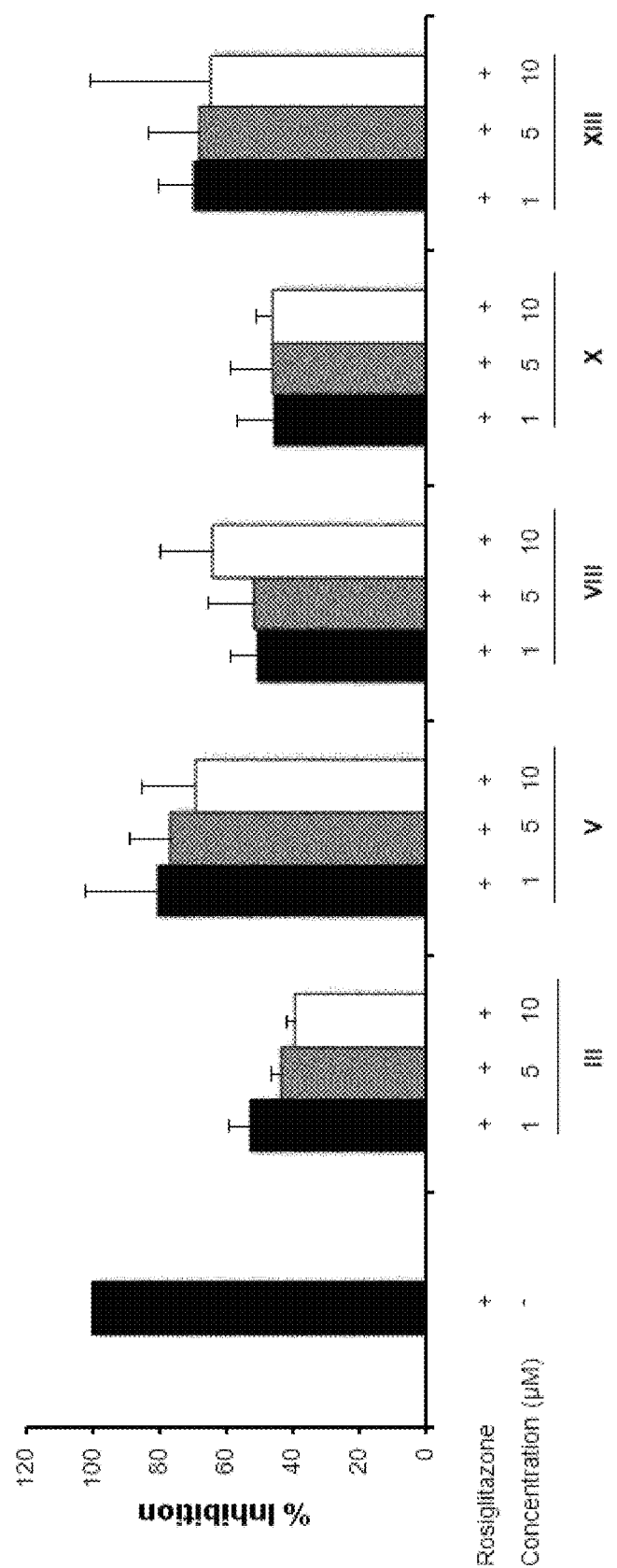

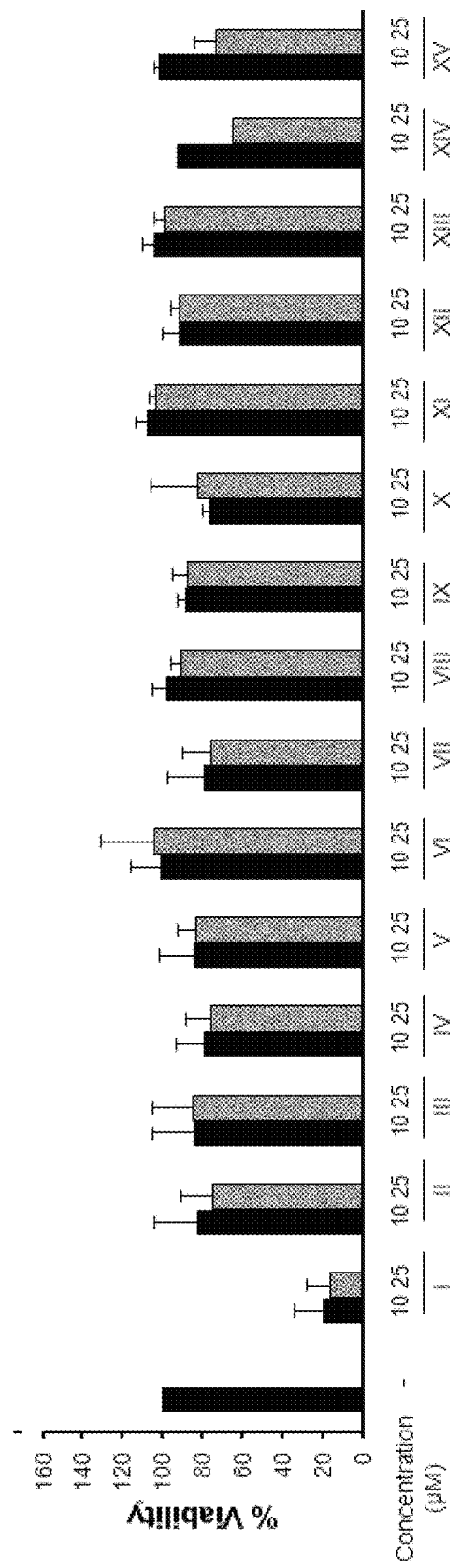

MO3.13

CANNABIDIOL QUINONE DERIVATIVES

FIELD OF THE INVENTION

The present invention relates to novel cannabidiol quinone derivatives, and the synthesis of those compounds. Furthermore, the present invention relates to their use as a medicament and in therapy, particularly as peroxisome proliferator-activated receptor gamma (PPARg) modulators, for treating diseases and conditions responsive to PPARg modulation. This invention also provides pharmaceutical compositions comprising said compounds and method of treating diseases with said compounds.

BACKGROUND OF THE INVENTION

Nuclear receptors (NRs) are a major target of drug discovery. NRs are ligand-dependent transcription factors that possess the ability to directly interact with DNA regulating the transcriptional activity of their target genes. These receptors play essential roles in development, cellular homeostasis and metabolism, and they have been implicated in a wide range of diseases and, as such, have been the focus of drug development efforts for the pharmaceutical industry. In the newest nomenclature for nuclear receptors, the subfamily 1 C (NR1C) comprises three subtypes of mammals Perixome Proliferator Activated Receptors (PPARs): PPARα (also called NR1C1), PPARβ/δ (also called NR1C2) and PPARγ (also called PPARg, glitazone receptor or NR1C3). PPARs control the expression of networks of genes involved in adipogenesis, lipid metabolism, inflammation and maintenance of metabolic homeostasis [Barish et al., 2006]. PPARs activate gene transcription by binding to elements of DNA sequences, known as peroxisome proliferator response elements (PPRE) in the regulatory region of PPAR target genes [Poulsen et al., 2012]. In addition, PPARs negatively regulate the transcription of inflammatory response genes by antagonizing the Activator Protein-1 (AP-1), Nuclear Factor-kappa B (NF-kB), signal transducer and activator of transcription 3 (STAT3) and Nuclear Factor of Activated T-cells (NFAT) signaling pathways [Vanden Berghe et al. 2003].

Among PPARs, PPARg is of special interest because it is involved in the regulation of adipocyte formation, insulin sensitivity and inflammation [Fievet et al. 2006] [Stienstra et al. 2007] [Tontonoz and Spiegelman, 2008]. PPARg is expressed in a range of tissues including adipose tissue, skeletal muscle cells, osteoclasts, osteoblasts, immune cells, and in the central and peripheral nervous system. It is clear that PPARg is the dominant or "master" regulator of adipogenesis, due to the fact that is both sufficient and necessary for fat cell differentiation. The regulatory regions of a large number of genes that play important roles in lipogenesis and insulin sensitivity such as aP2, LPL, adiponectin, and Glut4 contain binding sites for PPARg [Rosen and MacDougald, 2006]. Therefore, activation of PPARg in adipose tissue impacts whole-body insulin sensitivity.

In addition to its role in metabolic homeostasis regulation, emerging effects of PPARg have been reported including anti-inflammatory, anti-tumor and anti-fibrotic potentials especially [Zhao et al., 2006]. TGFb/Smad signaling blockage by PPARg activation leads to decreased collagen deposition in hepatic, pulmonary, and renal fibrosis [Ferguson et al., 2009] [Wang et al., 2007] [Zhang et al., 2009]. On the other hand, activation of PPARg exerts anti-inflammatory activities in several cell types by inhibiting the expression of pro-inflammatory genes, thereby reducing the production of cytokines, metalloproteases and acute-phase proteins [Tontonoz and Spiegelman, 2008]. It also acts increasing anti-inflammatory cytokines, and inhibiting inducible nitric oxide synthase (iNOS) expression [Széles et al., 2007]. Interestingly, PPARg agonists have shown anti-inflammatory and neuroprotective effects in several experimental models of Parkinson's diseases, amyotrophic lateral sclerosis, multiple sclerosis and stroke, as well as in a few clinical studies [Bernardo and Minghetti, 2008]. In this sense it has been shown that PPARg is highly expressed in retinoic acid treated neuronal precursors (NP) and it is involved in two stages of neural differentiation of mouse embryonic stem cells, during and post-NPs formation [Ghoochani et al., 2012]. Additionally, PPARg must formally be considered a tumor suppressor gene in the genetic sense. It is expressed in a variety of tumor cells, and the activation of PPARg by ligands led to either inhibition of cell proliferation or induction of apoptosis [Tachibana et al., 2008] [Tontonoz and Spiegelman, 2008].

The beneficial effects of PPARg activation by specific ligand agonists can be used for the treatment of several chronic diseases such as diabetes, atherosclerosis, rheumatoid arthritis, liver fibrosis, inflammatory bowel diseases, nephropathy, psoriasis, skin wound healing, scleroderma (SSc) neurodegenerative and neuroinflammatory disorders, and cancer.

Among activators of PPARg ligands, the thiazolidindiones (TZDs) are of most clinical importance [Lehmann et al., 1995]. For this reason rosiglitazone and pioglitazone have been largely used so far in the clinical practice. They provide similar effects on glycemic control, as well as a range of similar adverse effects, such as weight gain, fluid retention, and increased risk of hearth failure, which seem to be PPARg mediated. Indeed, rosiglitazone was recently withdrawn in Europe and its use has been restricted in USA as a consequence of increased risk of cardiovascular events in type 2 diabetic patients.

Although TZDs are potent PPARg full agonists (PPARg-fa) their mechanism-based side effects have limited the full therapeutic potential of those compounds [Gelman et al., 2007] [Ciudin et al., 2012]. But the physiologic and therapeutic relevance of the PPARg pathway have promoted new studies to develop newer classes of molecules that reduce or eliminate adverse effects [Ahmadian et al., 2013]. Therefore, much progress has been achieved in the discovery and development of selective PPARg modulators (PPARg-m) as safer alternatives to PPARg-fa. The preclinical and clinical findings clearly suggest that selective PPARg-m have the potential to become the next generation of PPARg agonists: effective insulin sensitizers with a superior safety profile to that of PPARg-fa. [Doshi et al. 2010].

In this sense natural and synthetic cannabinoids are considered PPARg-m that alleviates inflammatory process through activation of PPARg. Some examples of cannabinoid-based PPARg-m are ajulemic acid [Liu et al., 2003], [Burstein S. 2005], WIN55212-2 [Sun and Bennett, 2007], $^9$Δ-THC and CBD [O'Sullivan 2007], and CBG [Granja et al., 2012].

Some cannabinoid quinone derivatives such as CBD-Q (HU-311, also named VCE-004 in the present invention) and CBG-Q (VCE-003) have been described [Kogan et al., 2004] [Granja et al., 2012]. Interestingly, VCE-004 (also known as HU-331) showed an EC50 of 5 µM, thus presenting four times higher binding affinity than its parent molecule CBD (EC50 of 21 µM), and VCE-003 showed a significantly enhanced binding affinity for PPARg (EC50 2.2 µM) compared to its parent molecule CBG (EC50 12.7 µM)

[Granja et al., 2012]. Other CBD quinones such as CBD-1,4-dihydroxyquinone, 4 methyl-CBD-quinone and 4-formylmethoxy-CBD-quinone have been also described and showed higher affinity for PPARg compared to its parent molecule CDB [WO2011117429 A1]. However the synthesis of those compounds it is very difficult to reproduce and the compounds are very unstable making them impossible for pharmaceutical development.

Quinones represent a class of toxicological intermediates, which can create a variety of hazardous effects in vivo, including acute cytotoxicity and immunotoxicity [Bolton et al., 2000]. The mechanisms by which quinones cause these effects can be quite complex. Quinones are Michael acceptors, and cellular damage can occur through alkylation of crucial cellular proteins and/or DNA. Alternatively, quinones are highly redox active molecules which can redox cycle with their semiquinone radicals, leading to formation of reactive oxygen species (ROS) that can cause severe oxidative stress within cells through the formation of oxidized cellular macromolecules, including lipids, proteins, and DNA [Monks and Jones, 2012]. Although there are numerous examples of quinone-based compounds with therapeutic use, the concerns over non-specific toxicity and lack of selectivity, the Michael acceptor motif is rarely introduced by design in drug leads.

The Keap1-Nrf2 pathway is the major regulator of cytoprotective responses to endogenous and exogenous stresses caused by reactive oxygen species (ROS) and electrophiles. The key signaling proteins within the pathway are the transcription nuclear factor (erythroid-derived 2)-like 2 (Nrf2) that binds together with small Maf proteins to the antioxidant response element (ARE) in the regulatory regions of target genes. Under basal conditions Nrf2 is retained in the cytoplasm by the inhibitor Keap1 (Kelch ECH associating protein 1). When cells are exposed to oxidative stress, electrophiles, or chemopreventive agents, Nrf2 escapes Keap1-mediated repression and activates antioxidant responsive element (ARE)-dependent gene expression to maintain cellular redox homeostasis [Na and Surh, 2013].

Nrf2 can protect cells and tissues from a variety of toxicants and carcinogens by increasing the expression of a number of cytoprotective genes. Just as Nrf2 protects normal cells, studies have shown that Nrf2 may also protect cancer cells from chemotherapeutic agents and facilitate cancer progression [Na and Surh 2013]. Cancer cells survive persistent endogenous oxygen-mediated stress and become resistant to certain anticancer agents that exert cytotoxicity through ROS production. Under such conditions, an active Nrf2 pathway could maintain a favorable redox balance in cancer cells by keeping ROS levels within a range that promotes their growth and survival. Sustained accumulation or activation of Nrf2 is speculated to confer on a subset of premalignant or cancerous cells an advantageous environment to proliferate, evade apoptosis, metastasize, and tolerate therapeutic intervention.

Inhibition of Nrf2 overexpression has been known to reverse the phenotypic characteristics of cancer cells, lending support to this supposition [Sporn and Liby, 2012]. Constitutive overactivation of Nrf2 has been observed in numerous types of malignancies, such as squamous cell carcinomas, lung cancer, breast cancer, gallbladder cancer, prostate cancer, renal cancer, ependymomas, ovarian epithelial carcinoma, endometrial cancer, and pancreatic cancer [Na and Surh, 2013]. Cancer patients with a constitutively elevated level of Nrf2 expression in their tumor, in general, show a lower survival rate [Solis et al., 2010]. Therefore, Nrf2 activation is considered a prognostic molecular marker for determining the status of cancer progression and contributes to both intrinsic and acquired chemoresistance. Thus, this antioxidant transcription factor may also act as a proto-oncogene and enhanced Nrf2 activity promotes formation and chemoresistance of solid cancers [Sporn and Liby, 2012].

To improve just PPARg agonistic activity, but without inducing activation of Nrf2 in order to avoid potential side effects, present invention has developed a library of novel compounds starting from VCE-004 and Cannabidiol acid (CBDA) as templates and surprisingly it has been found CBD-quinone derivatives (CBD-Q derivatives) with specific modifications in position 3 resulted on novel compounds with high PPARg agonistic effect but lacking electrophilic (Nrf2 activation) and cytotoxic activities. Therefore, the novel compounds are suitable for treating chronic diseases responsive to PPARg modulation.

VCE-004 (compound I), precursor of the CBD-Q derivatives II to X of present invention is an agonistic PPARg ligand that also activates the transcription factor Nrf2, a cellular sensor of oxidative/electrophilic stress reflecting the generation of ROS in VCE-004-treated cells. Therefore chronic treatment with this type of CBD-Q derivatives that activate the Nrf2 pathway may result in tumor promotion, as explained above. In addition, chromenopyrazolediones, which are structural analogues of CBD-Q, induce cytotoxicity in prostate cancer cells through induction of reactive oxigen species (ROS) and PPARg-dependent mechanisms [Morales et al., 2013]. Thus, oxidation of CBD molecule results in a class of CBD-Q compounds such as VCE-004 that activate PPARg and also induce ROS-mediated Nrf2 activation.

Those CBD-Q derivatives of present invention are different from the compounds described by Kogan et al. [Kogan et al., 2004] and Morales et al. [Morales et al., 2013] since the modifications in position 3 confers to the compounds of the present invention the capacity to activate to PPARg and to protect from glutamate-induced cytotoxicity without activating Nrf2. Moreover, CBD-Q derivatives with modifications in position 3 also inhibited TGFb-induced collagen gene transcription and collagen expression. The compounds described in the present invention are also different from the compounds described in WO20011117429, which are unstable, difficult to synthesize and never tested for Nrf2 activation. The CBD-Q derivatives described in the present invention also shown a remarkable low cytotoxicity in cell lines of neuronal origin compared to VCE-004 (compound I) comprised in the state of the art.

SUMMARY OF THE INVENTION

Departing from the prior art, the problem of the present invention is to provide novel cannabidiol-quinone derivatives (CBD-Q derivatives) with exhibits activity in modulating PPARg without inducing Nrf2 activation and cytotoxicity.

More specifically, in the present invention compounds are derivatives of cannabidiol-quinone derivatives (CBD-Q derivatives) of Formula (I):

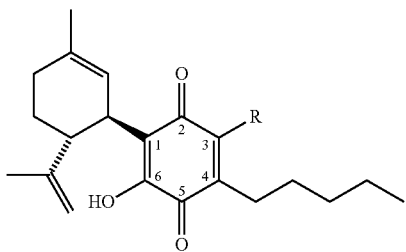

(I)

wherein R is the carbon atom of a linear or branched group, represented by: alkyl, aryl, alkenyl, alkynyl, acyl, or alkoxycarbonyl groups; or wherein R is the nitrogen atom of a linear or branched group, represented by: alkylamine, arylamine, alkenylamine or alkynylamine groups. The quinone ring has been numbered arbitrarily in order to show in which position of the ring the substituents replacement is made for rendering the CBD-Q derivatives of present invention. As far as IUPAT nomenclature might allow it, the numbering of quinone ring has been maintained (see derivatives of formula II to X, wherein position 3 of said quinone ring was the position where all substituents replacement occurred and the nomenclature of the aforesaid derivatives matched and reflected that fact). However, when the substituents groups bound to position 3 of quinone ring, altered the numbering of the positions of the aforesaid quinone ring obliged by IUPAT nomenclature, the outcoming nomenclature was used although, only in appearance, replacement in position 3 of quinone ring was apparently missed, what was not really the case, as shown by graphic formula of derivatives represented by formula XI to XV.

In a preferred embodiment, the compounds of the invention are those of Formula (II), (III), (IV), (V), (VI), (VII), (VIII), (X), (XI), (XII), (XIII), (XIV) and (XV).

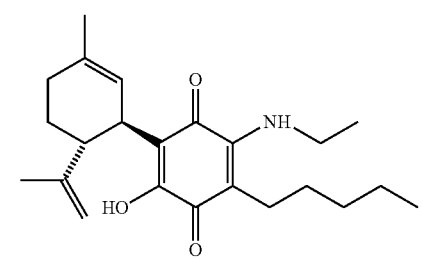

(II)

(1'R,6'R)-3-(Ethylamine)-6-hydroxy-3'-methyl-4-pentyl-6'-(prop-1-en-2-yl)-[1,1'-bi(cyclohexane)]-2',3,6-triene-2,5-dione

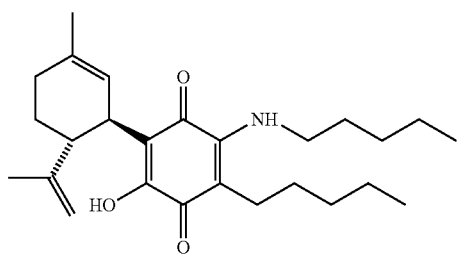

(III)

(1'R,6'R)-3-(Pentylamine)-6-Hydroxy-3'-methyl-4-pentyl-6'-(prop-1-en-2-yl)-[1,1'-bi(cyclohexane)]-2',3,6-triene-2,5-dione

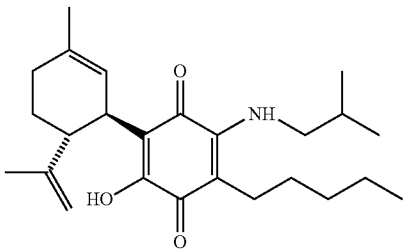

(IV)

(1'R,6'R)-3-(Isobutylamine)-6-Hydroxy-3'-methyl-4-pentyl-6'-(prop-1-en-2-yl)-[1,1'-bi(cyclohexane)]-2',3,6-triene-2,5-dione

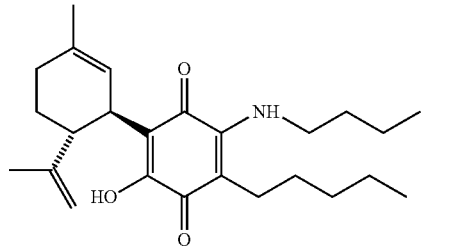

(V)

(1'R,6'R)-3-(Butylamine)-6-hydroxy-3'-methyl-4-pentyl-6'-(prop-1-en-2-yl)-[1,1'-bi(cyclohexane)]-2',3,6-triene-2,5-dione

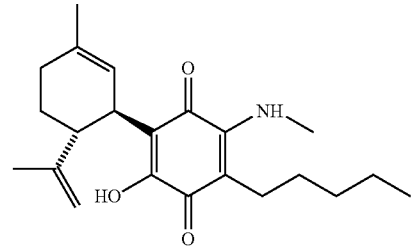

(VI)

(1'R,6'R)-3-(Methylamine)-6-Hydroxy-3'-methyl-4-pentyl-6'-(prop-1-en-2-yl)-[1,1'-bi(cyclohexane)]-2',3,6-triene-2,5-dione

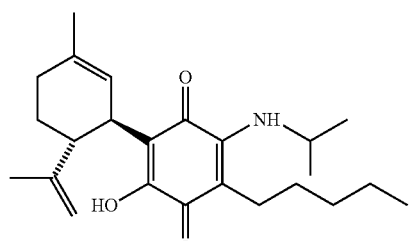

(VII)

(1'R,6'R)-3-(Isopropylamine)-6-Hydroxy-3'-methyl-4-pentyl-6'-(prop-1-en-2-yl)-[1,1'-bi(cyclohexane)]-2',3,6-triene-2,5-dione

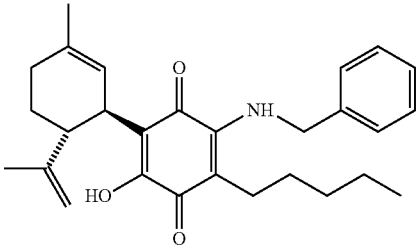

(VIII)

(1'R,6'R)-3-(Benzylamine)-6-hydroxy-3'-methyl-4-pentyl-6'-(prop-1-en-2-yl)-[1,1'-bi(cyclohexane)]-2',3,6-triene-2,5-dione (IX)

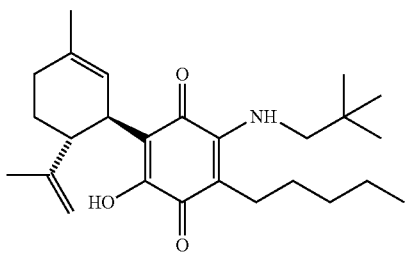

(1′R,6′R)-3-(Neopentylamine)-6-hydroxy-3′-methyl-)-4-pentyl-6′-
(prop-1-en-2-yl)-[1,1′-bi(cyclohexane)]-2′,3,6-triene-2,5-dione (X)

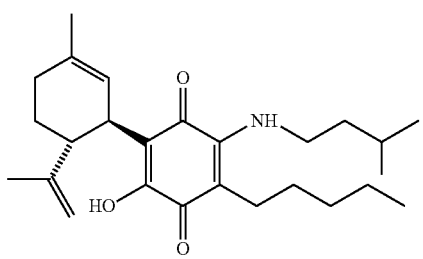

(1′R,6′R) 3-(Isopentylamine)-6-Hydroxy-amine-3′-methyl-4-pentyl-6′-
(prop-1-en-2-yl)-[1,1′-bi(cyclohexane)]-2′,3,6-triene-2,5-dione (XI)

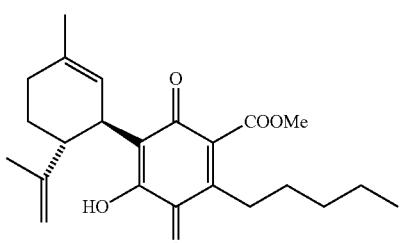

Methyl 4-hydroxy-5-((1R,6R)-3-methyl-6-(prop-1-en-2-yl)
cyclohex-2-enyl)-3,6-dioxo-2-pentylcyclohexa-1,4-dienecarboxylate (XII)

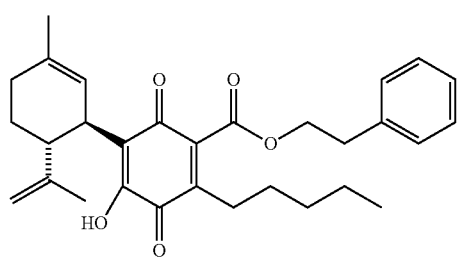

Phenylethyl 4-hydroxy-5-((1R,6R)-3-methyl-6-(prop-1-en-2-yl)
cyclohex-2-enyl)-3,6-dioxo-2-pentylcyclohexa-1,4-dienecarboxylate (XIII)

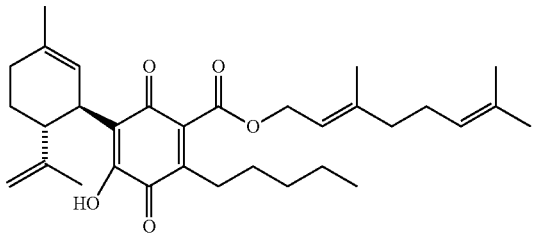

(E)-3,7-Dimethylocta-2,6-dienyl-4-hydroxy-5-((1R,6R)-3-methyl-
6-(prop-1-en-2yl)cyclohex-2-enyl)-3,6-dioxo-2-pentylcyclohexa-1,4-
dienecarboxylate (XIV)

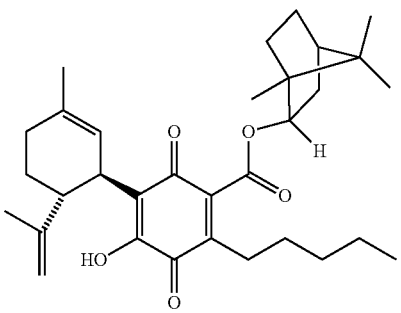

(1R,4S)-1,7,7-Trimethylbicyclo[2.2.1]heptan-2-yl-4-hydroxy-5-
((1R,6R)-3-methyl-6-(prop-1-en-2-yl)cyclohex-2-enyl)-3,6-dioxo-2-
pentylcyclohexa-1,4-dienecarboxylate (XV)

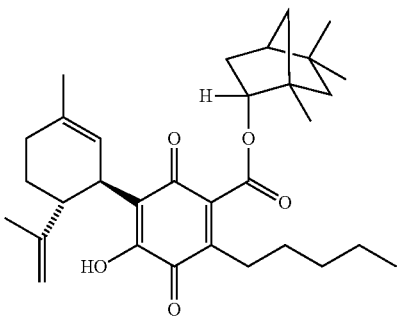

(1R,2R,4R)-1,5,5-trimethylbicyclo[2.2.1]heptan-2-yl 4-hydroxy-5-
((1R,6R)-3-methyl-6-(prop-1-en-2-yl)cyclohex-2-enyl)-3,6-dioxo-2-
pentylcyclohexa-1,4-dienecarboxylate VCE-004 (compound I) precursor of the CBD-Q derivatives II to X of Formula I of present invention can be easily synthesized from CBD (THC Pharma, Germany; ref: THC-1073G-10).

Compounds XI to XV of the present invention can be synthesized by starting from the natural cannabinoids CBDA (cannabidiol acid) (THC Pharma, Germany; ref: THC-1232-100) by means of the substitution of some specific radicals.

As it will be inferred below from the examples and figures, the modifications in position 3′ comprised in the general Formula I confer the compounds of the present invention the capacity to activate to PPARg, to protect from glutamate-induced cytotoxicity and to inhibit TGFb-induced collagen production. These compounds also shown a remarkable low cytotoxicity in cell lines of neuronal origin compared with VCE-004 comprised in the state of the art.

The compounds of the invention also comprise their analogs, derivatives, tautomeric forms, isomers, stereoisomers, polymorphs, pharmaceutically acceptable salts, pharmaceutically acceptable solvates, and compositions containing the same.

For the purposes of present description the term "analogue/s" refers to any entity structurally derived or homologous to the compounds of formula (I).

In the context of this invention "derivative/s" of the compounds of formula (I) should be interpreted as any CBD-quinone analogue, always substituted in position 4' and showing the pharmacological properties linked to that substitution in position 4', as defined herein, but also having moieties replacements in other positions of the CBD-Q molecule, different to the groups shown in said formula (I).

The term "tautomers" are constitutional isomers of organic compounds that readily interconvert by a chemical process (tautomerization).

The term "isomers" or "stereoisomers" refers to compounds, which have identical chemical constitution, but differ with regard to the arrangement of the atoms or groups in space.

As used herein "polymorph" refers to crystalline forms having the same chemical composition but different spatial arrangements of the molecules, atoms, and/or ions forming the crystal.

The term "pharmaceutically acceptable salt" refers to any pharmaceutically acceptable salt, which upon administration to the patient is capable of providing (directly or indirectly) a compound as described herein. Such salts preferably are acid addition salts with physiologically acceptable organic or inorganic acids. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts. However, it will be appreciated that non-pharmaceutically acceptable salts also fall within the scope of the invention since those may be useful in the preparation of pharmaceutically acceptable salts. Procedures for salt formation are conventional in the art.

The term "solvate" in accordance with this invention should be understood as meaning any form of the active compound in accordance with the invention in which said compound is bonded by a non-covalent bond to another molecule (normally a polar solvent), including especially hydrates and alcoholates.

A further embodiment of the present invention refers to the use of compounds of Formula (I) or derivatives thereof as medicaments, particularly as PPARg agonists of the PPARg receptors, which do not induce Nfr2 activation, particularly in the treatment of diseases such as atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity, type II diabetes, and other diseases that can be treated with PPARg agonists.

Other embodiment of the present invention refers to the use of compounds of Formula (I) for the manufacture of a composition for treating PPRAg related diseases with lower citotoxicity such as atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity, type II diabetes, and other diseases that can be treated with PPARg agonists.

An alternative embodiment of the present invention refers to the use of the above mentioned compounds of Formula (I) or derivatives, alone or formulated in compositions, particularly pharmaceutical compositions, that comprise at least one of the compounds of the invention combined with at least another active compound having additive or synergistic biological activities. Alternatively said compositions can be formulated with at least one inert ingredient as a carrier or excipient such as: cosolvents, surfactants, oils, humectants, emollients, preservatives, stabilizers and antioxidants. Any pharmacologically acceptable buffer may be used, e. g., TRIS or phosphate buffers.

For the purposes of present description the term "active compound or active principle" should be taken as synonyms and mean a chemical entity which exerts therapeutic effects when administered to human or animal beings.

Typical compositions include the compounds of the invention, or derivatives thereof, associated with pharmaceutically acceptable excipients, which may be a carrier or a diluent, as a way of example. Such compositions can be in the form of a capsule, sachet, paper or other container. In making the compositions, conventional techniques for the preparation of pharmaceutical compositions may be used. For example, the compound of interest will usually be mixed with a carrier, or diluted by a carrier, or enclosed within a carrier that may be in the form of an ampoule, capsule, sachet, paper, or other container. When the carrier serves as a diluent, it may be solid, semi-solid, or liquid material that acts as a vehicle, excipient, or medium for the active compound. The compound of interest can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The composition could be used for the treatment of diseases such as atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity, type II diabetes, and other diseases that can be treated with PPARg agonists.

One preferred embodiment of the present invention refers to the route of administration, that may be any route which effectively transports the compound of interest to the appropriate or desired site of action, such as oral, nasal, topical, pulmonary, transdermal or parenteral, e. g., rectal, subcutaneous, intravenous, intraurethral, intramuscular, intranasal, ophthalmic solution or an ointment.

For nasal administration, the preparation may contain the compound of interest dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine), or cyclodextrin, or preservatives such as parabens.

To prepare topical formulations, the compound of interest is placed in a dermatological vehicle as is known in the art. The amount of the compound of interest to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the compound of interest and selects the amount of formulation administered, depending upon clinical experience with the patient in question or with similar patients.

For ophthalmic applications, the compound of interest is formulated into solutions, suspensions, and ointments appropriate for use in the eye. The concentrations are usually as discussed above for local preparations.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers.

Capsules are prepared by mixing the compound of interest with an inert pharmaceutical diluent, and filling the mixture into a hard gelatin capsule of appropriate size. Soft gelatin capsules are prepared by machine encapsulation of slurry of the compound of interest with an acceptable vegetable oil, light liquid petrolatum or other inert oil. Fluid unit dosage forms for oral administration such as syrups, elixirs and suspensions can be prepared. The water-soluble forms can be dissolved in an aqueous vehicle together with sugar, aromatic flavoring agents and preservatives to form syrup. An elixir is prepared by using a hydroalcoholic (e. g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill, such as the use of suitable injectable solutions or suspensions. The formulation, which is sterile, is suitable for various topical or parenteral routes including intra-dermal, intramuscular, intravenous, and subcutaneous.

In addition to the compound of interest, the compositions may include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination.

Examples of such diluents that are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or non-toxic, non-therapeutic, non-immunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives, and excipients are those amounts that are effective to obtain a pharmaceutically acceptable formulation in terms of solubility, biological activity, etc.

The compound of interest may be incorporated into a microsphere. The compound of interest can be loaded into albumin microspheres, from which it is possible to recover such microspheres in a dry powder for nasal administration. Other materials suitable for the preparation of microspheres include agar, alginate, chitosan, starch, hydroxyethyl starch, albumin, agarose, dextran, hyaluronic acid, gelatin, collagen, and casein. The microspheres can be produced by various processes known to the person skilled in the art such as a spray drying process or an emulsification process.

For example, albumin microspheres can be prepared by adding rabbit serum albumin in phosphate buffer to olive oil with stirring to produce water in oil emulsion. Glutaraldehyde solution is then added to the emulsion and the emulsion stirred to cross-link the albumin. The microspheres can then be isolated by centrifugation, the oil removed and the spheres washed, e. g., with petroleum ether followed by ethanol. Finally, the microspheres can be sieved and collected and dried by filtration.

Starch microspheres can be prepared by adding a warm aqueous starch solution, e. g. of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles. These particles are then filtered off at room temperature and slurred in a solvent such as ethanol, after which the particles are again filtered off and laid to dry in air. The microspheres can be hardened by well-known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate, and borate. Dialdehydes are used to cross-link proteins such as albumin by interaction with amino groups, and diketones form schiff bases with amino groups. Epichlorohydrin activates compounds with nucleophiles such as amino or hydroxyl to an epoxide derivative.

Another preferred embodiment of the invention is the dosage scheme. The term "unit dosage form" refers to physically discrete units suitable as unitary dosages for subjects, e. g., mammalian subjects, e. g. humans, dogs, cats, and rodents, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described. The compositions can be included in kits, which can contain one or more unit dosage forms of the composition and instructions for use to treat one or more of the disorders described herein.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical, intraocular, oral, and parenteral routes.

An effective amount of the compound of interest is employed in treatment. The dosage of compounds used in accordance with the invention varies depending on the compound and the condition being treated for example the age, weight, and clinical condition of the recipient patient. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

A last embodiment of the present invention refers to a method for treating diseases such as atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity and Type II diabetes, which can be treated with PPARg agonists; that comprises the administration to the patient of an effective amount of the above composition.

ABBREVIATIONS

AP-1: Activator Protein-1
ARE: Antoxidant Responsive element
CBD: Cannabidiol.
CBDA: Cannabidiol acid.
CBD-Q: Cannabidiol quinone.
CBG-Q: Cannabigerol quinone (also named VCE-003).
DCC: Dicyclohexylcarbodiimide
Keap1: Ketch ECH associating protein 1.
NFAT: Nuclear Factor of Activated T-cells
NFE2L2 or (Nrf2): Nuclear factor (erythroid-derived 2)-like 2.
NF-kB: Nuclear Factor-kappa B
NP: Neuronal precursors
NR1C: Nuclear subfamily 1 C.
NRs: Nuclear receptors.
PPARs: Perixome proliferator activated receptors.
PPARg: Peroxisome proliferator-activated receptor gamma also called PPARγ, glitazone receptor or NR1C3.
PPARg-m: PPARg modulators
PPARg-fa: PPARg full agonist.
PPARα: Peroxisome proliferator-activated receptor alfa also called NR1C1.
PPARβ/δ: Peroxisome proliferator-activated receptor beta/delta also called NR1C2.
PPRE: Peroxisome proliferator response element.
ROS: Reactive oxygen species
STAT3: Signal transducer and activator of transcription 3
TGFb: Transforming growth factor beta
VCE-004: Cannabidiol quinone compound; also named HU-331 and compound I:
HU-331: Cannabidiol quinone compound; also named VCE-004 and compound I:

DESCRIPTION OF FIGURES

The figures of the invention are briefly described below. An in deep explanation of each figure is included in every pertinent example.

Figures Abbreviations

I: refers to VCE-004 (CBD-Q).
II: refers to compound of formula (II).
III: refers to compound of formula (III).
IV: refers to compound of formula (IV).
V: refers to compound of formula (V).
VI: refers to compound of formula (VI).
VII: refers to compound of formula (VII).
VIII: refers to compound of formula (VIII).
IX: refers to compound of formula (IX).
X: refers to compound of formula (X.
XI: refers to compound of formula (XI).
XII: refers to compound of formula (XII).
XIII: refers to compound of formula (XIII).
XIV: refers to compound of formula (XIV).
XV: refers to compound of formula (XV).

FIG. 1. PPARg transactivation assays in HEK-293 cells

The concentration of the tested compound (μM) is shown at the x-axis and the PPARg activation fold is shown at the y-axis. This figure shows the effect of VCE-004 (compound I) versus the effect of compounds XI and II to V (FIG. 1A) and versus the effect of compounds VI-X (FIG. 1B), and versus the effect of compounds XII-XV (FIG. 1C) on PPARg activity. The PPARg full agonist Rosiglitazone (RZG) 1 μM was used as comparative control. Fold activation level was calculated, taking the control sample (−), without the presence of any PPARg agonist or activating agent, as reference. Data are expressed as mean±S.D. of at least three independent experiments.

Figure 2:
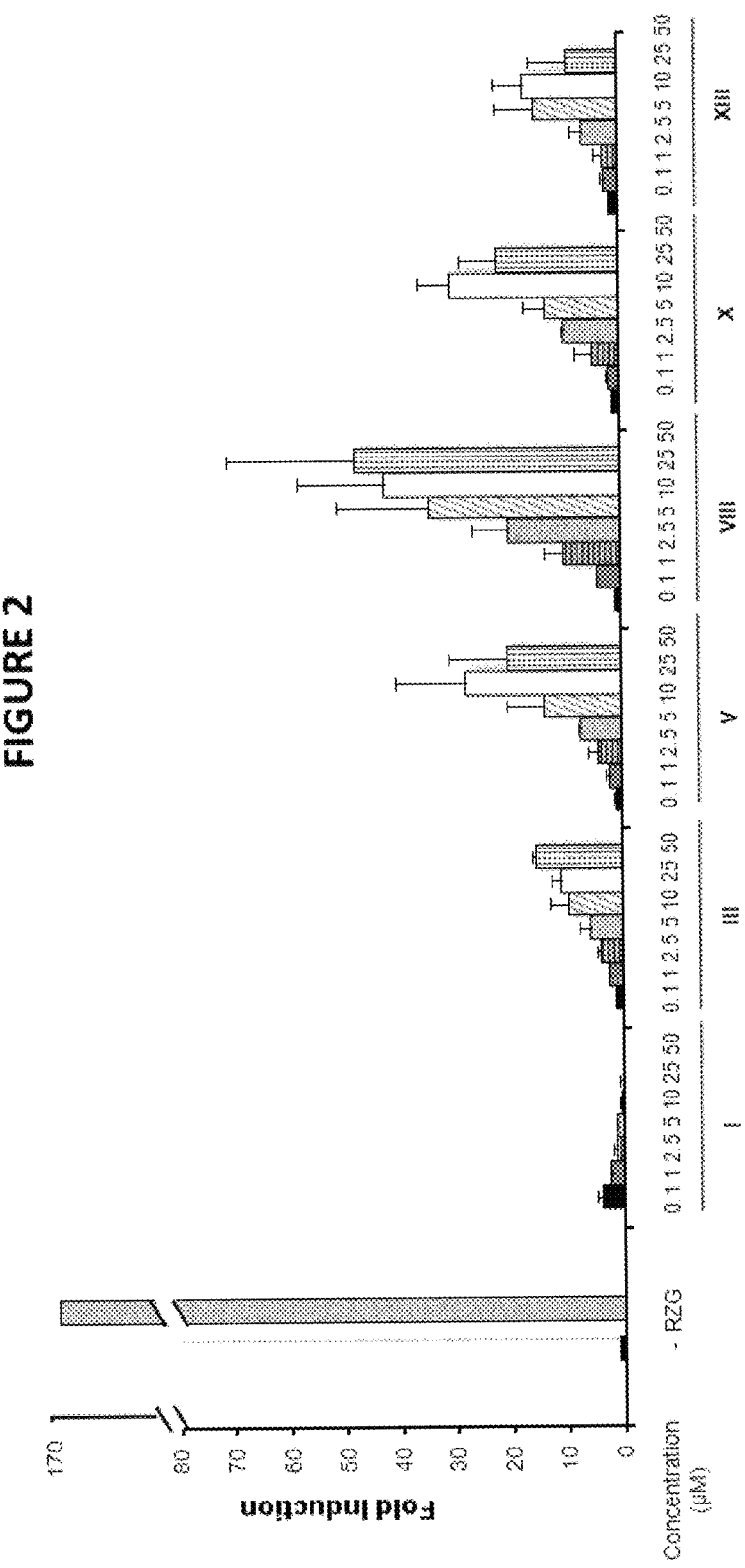

FIG. 2. PPARg transactivation assays in NIH-3T3 fibroblast cells.

The concentration of the tested compound (μM) is shown at the x-axis and the PPARg activation fold is shown at the y-axis. This figure shows the effect of VCE-004 (compound I) versus compounds III, V, VIII, X, and XIII on PPARg activity. The PPARγ full agonist Rosiglitazone (RZG) 1 μM was used as comparative control. Fold activation level was calculated, taking the control sample (−), without the presence of any PPARg agonist or activating agent, as reference. Data are expressed as mean±S.D. of at least three independent experiments.

Figure 3B:
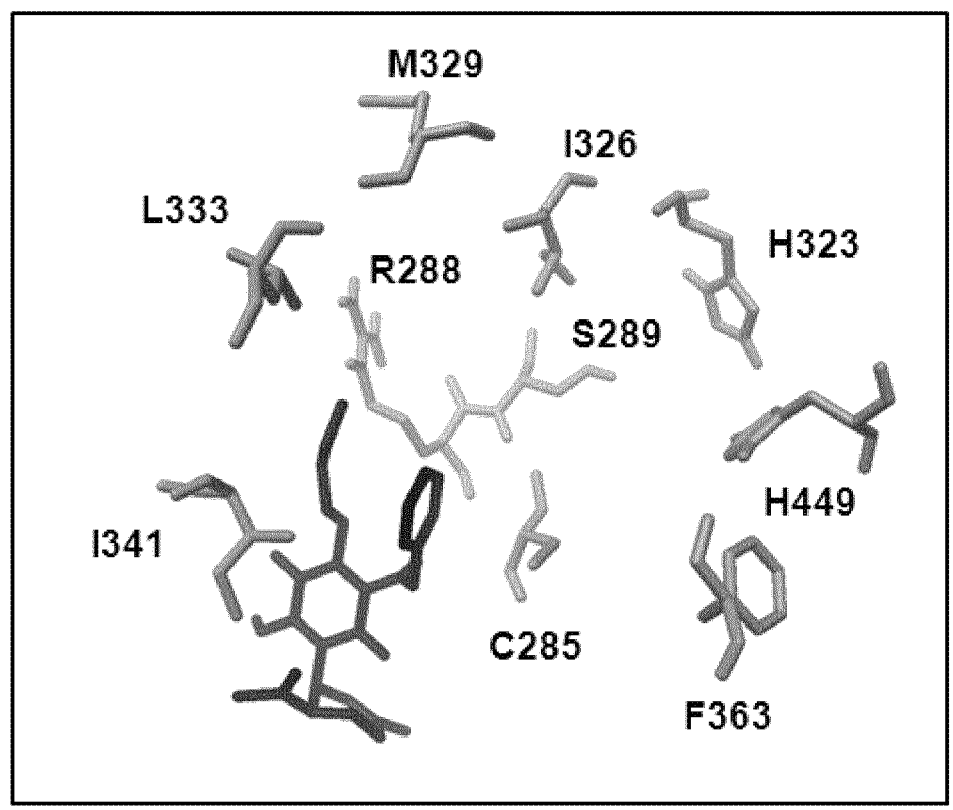

FIG. 3. CBD-quinone derivatives inhibit Rosiglitazone-induced PPARg activation.

(A) HEK-293 cells were co-transfected with GAL4-PPARg and GAL4-luc. Cells were pre-incubated for 30 min with the indicated doses of compounds III, V, VIII, X, and XIII, and then incubated for 6 hours with 1 μM Rosiglitazone (RSZ). Protein lysates were prepared and analyzed for luciferase activity. The concentration of the tested compound (µM) is shown at the x-axis and the PPARg activation fold is shown at the y-axis. This figure shows the effect of compounds III, V, VIII, X, and XIII on RSZ-induced PPARg activity Data are expressed as mean±S.D. of at least three independent experiments.

(B) Compound VIII binds to RSZ binding site on PPARg. Binding features of compound VIII (as an example) to PPARg were calculated by virtual docking, using the AutoDock software and setting the Vina algorithm as calculation system. Search space was set to find binding points all around the molecular surface. Compound VIII binds to PPARg in a closely related binding site for RSZ, but with a different ligand-receptor interaction pattern, leading to different conformational effect on the receptor.

Figure 4A:
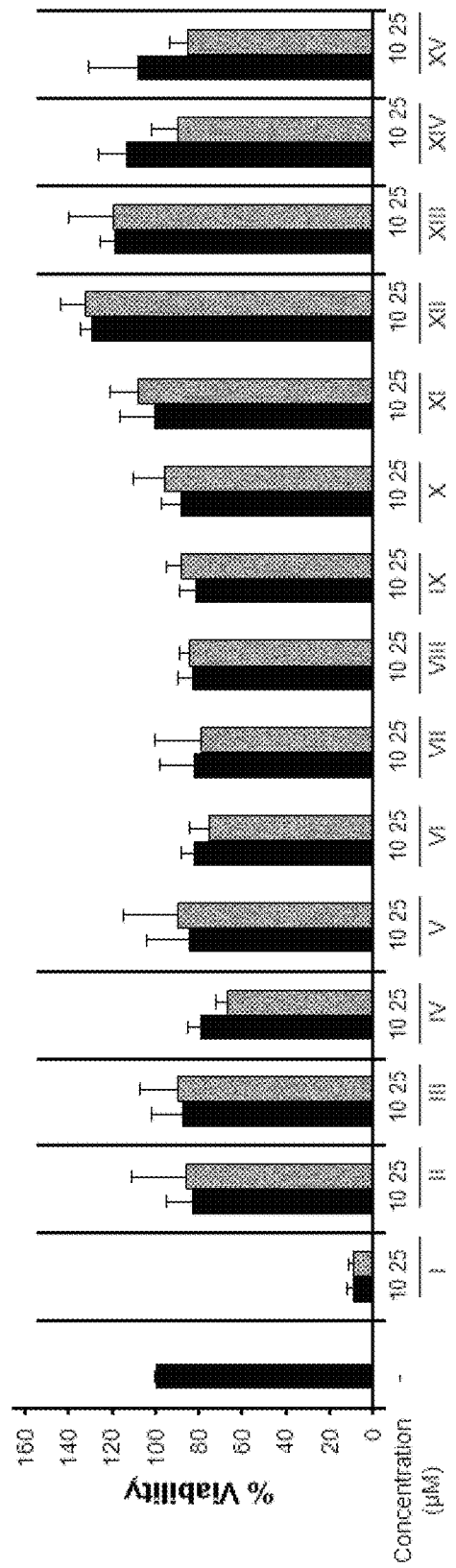
Figure 4C:
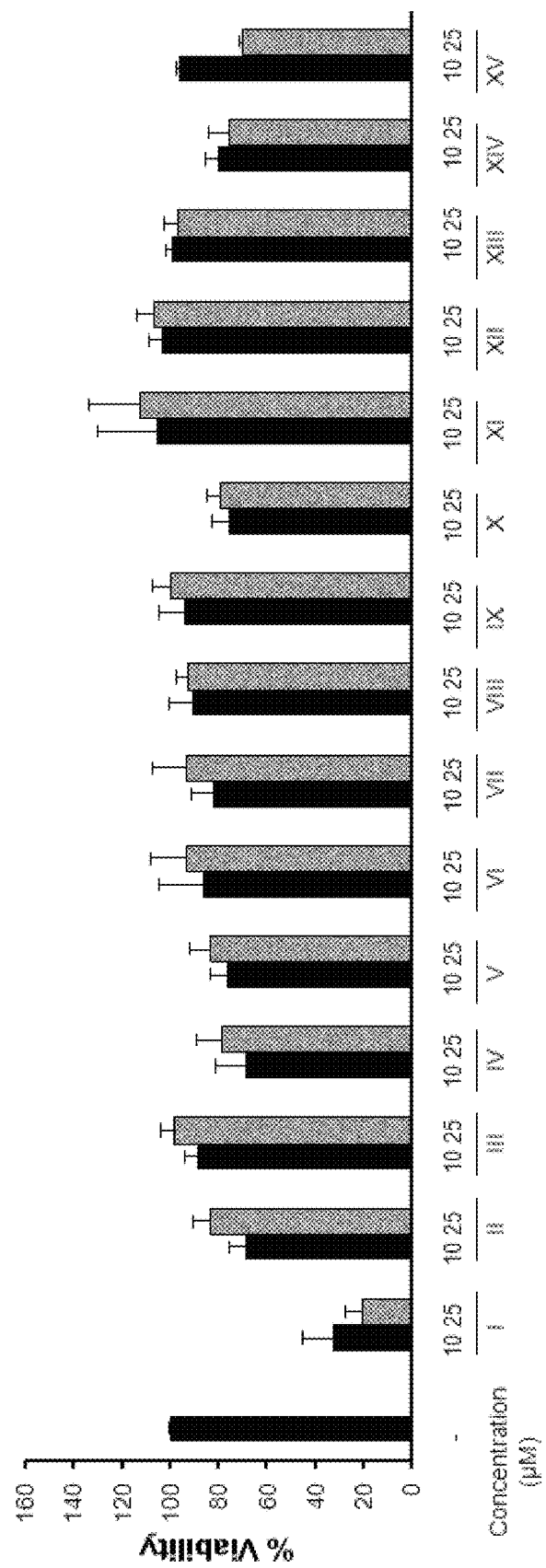

FIG. 4. Cytotoxicity activity.

The cell lines N2a (4A), HT22 (4B) and MO3.13 (4C) cells were incubated for 24 h with the indicated doses of VCE-004 (Compound I) versus compounds II to XV, and cell viability was quantified by MTT assay. Results are shown as mean±S.D. from at least three independent experiments, and expressed as percentage of cell viability against the control sample (−), without the presence of any PPARg agonist or activating agent. Control was set as 100% and data were referred to that value.

Figure 5:
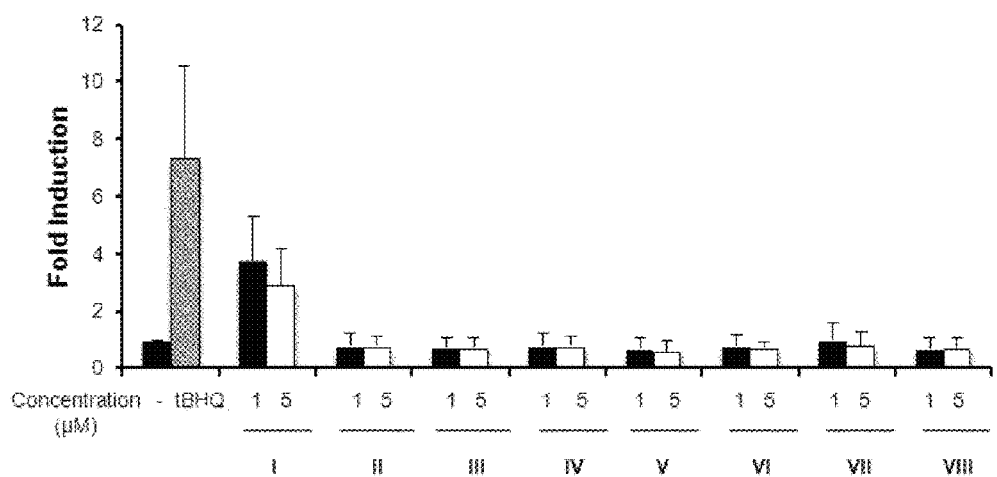
Figure 5:
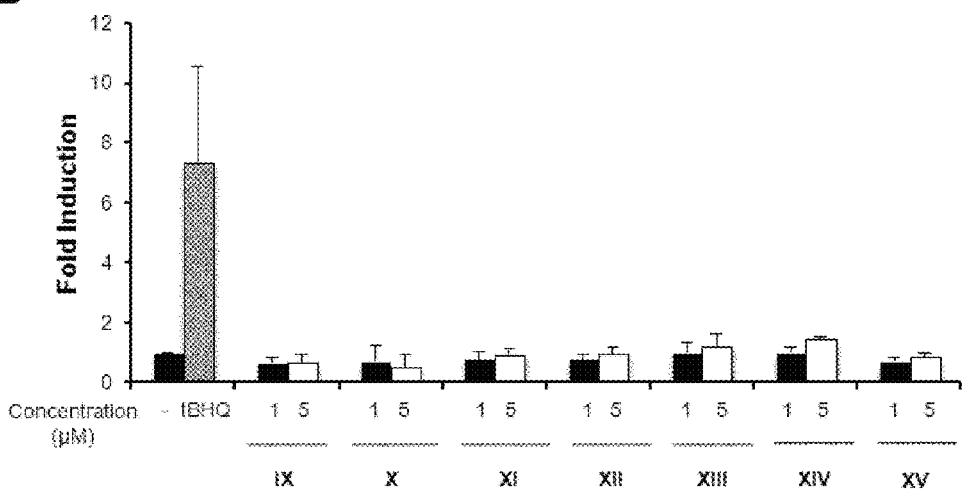

FIG. 5. Nrf2 transcriptional assays

HaCaT-ARE-Luc cells were incubated for 6 h with VCE-004 (compound I) and with compounds II to VIII (A) or with compounds IX to XV (B) at the indicated concentrations, and protein lysates were prepared and analysed for luciferase activity. The pro-oxidant tert-Butylhydroquinone (tBHQ) at 20 µM was used as positive control. Fold activation level was calculated, taking the control sample (−), without the presence of any PPARg agonist or activating agent, as reference. Data are expressed as mean±S.D. from at least three independent experiments.

Figure 6A:
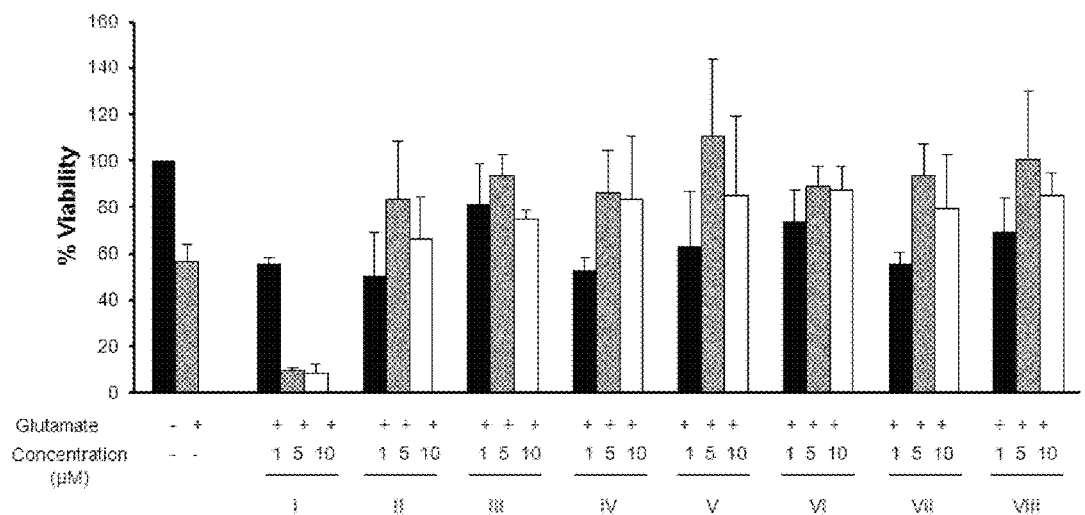
Figure 6B:
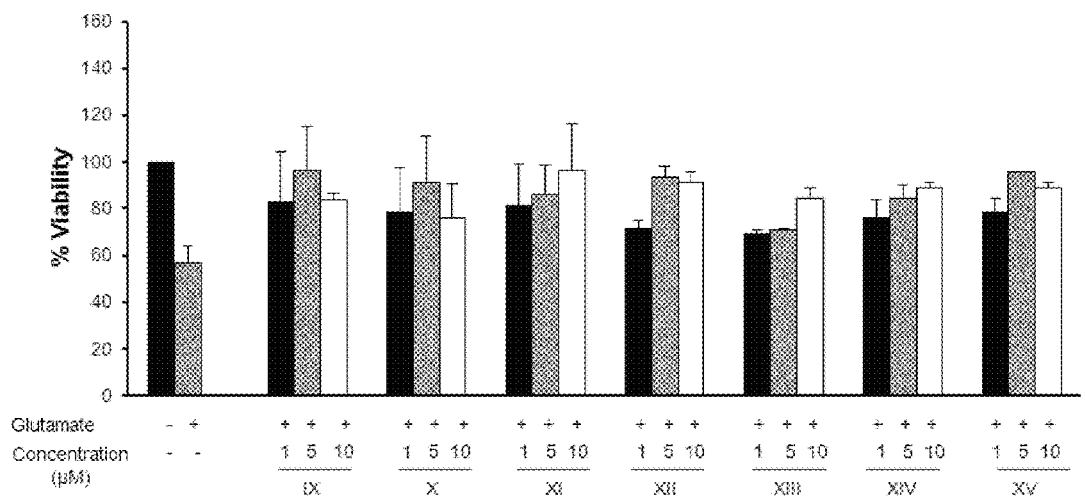

FIG. 6. Neuroprotective activity.

N2a cells were pre-incubated for 1 h with compounds I to VIII (5A) and IX to XV (5B) at the indicated concentrations. Then, cells were treated for 24 h with 5 mM glutamate to induce excitotoxicity. Cell viability was quantified by MTT assay. Results are shown as mean±S.D. from at least three independent experiments, and expressed as percentage of cell viability against the control sample (−), without the presence of any PPARg agonist or activating agent and with (+) or without (−) glutamate. Control was set as 100% and data were referred to that value.

Figure 7:
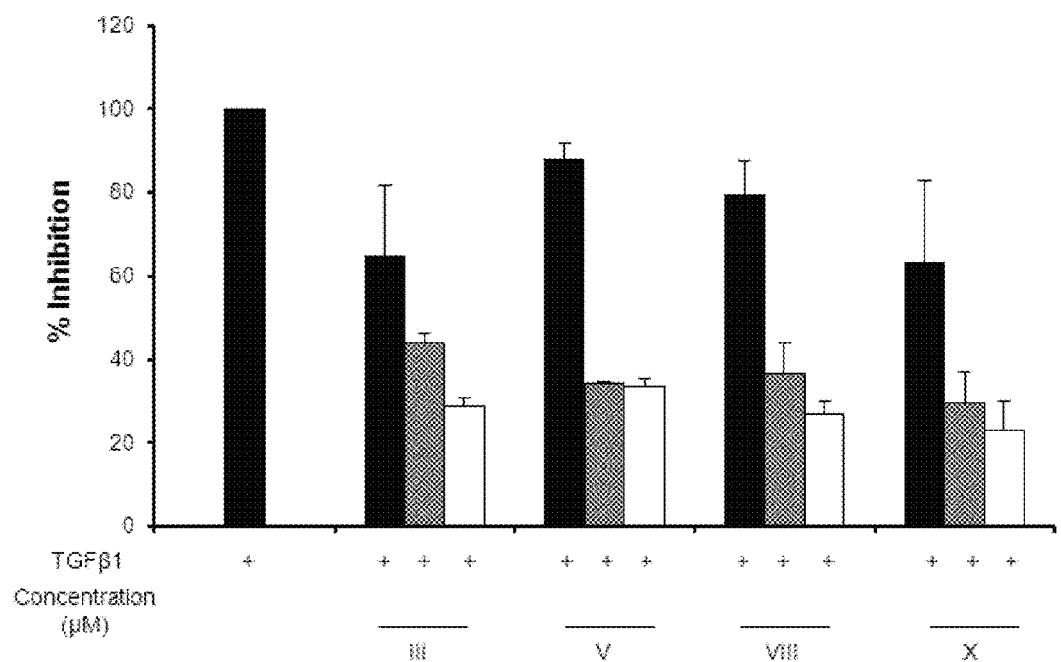

FIG. 7. Inhibition of TGFb-induced collagen type I gene transcription

To investigate the potential anti-fibrotic activity of CBD-derivatives NIH-3T3 fibroblast cells were transiently transfected with the plasmid COL1A2-Luc plasmid by using Roti©-Fect according to the manufacturer instructions. The COL1A2-luciferase construct contains sequences from −353 to +58 bp of the human COL1A2 promoter fused to the luciferase reporter gene (pGL2 basic, Promega, Madison, Wis.). Twenty-four hour later the cells were incubated with compounds III, V, VIII and X (taken as demonstrative examples among the whole family con CBD-Q derivatives represented by formulas II to XV) for 30 min and treated with TGFb (50 ng/ml) for 6 h. Protein lysates were prepared and analyzed for luciferase activity. The concentration of the tested compound (µM) is shown at the x-axis and the percentage of COL1A2 activation is shown at the y-axis considering 100% activation the effect of TGFb in the absence of the compounds. Data are expressed as mean±SD of at least three independent experiments.

Figure 8:
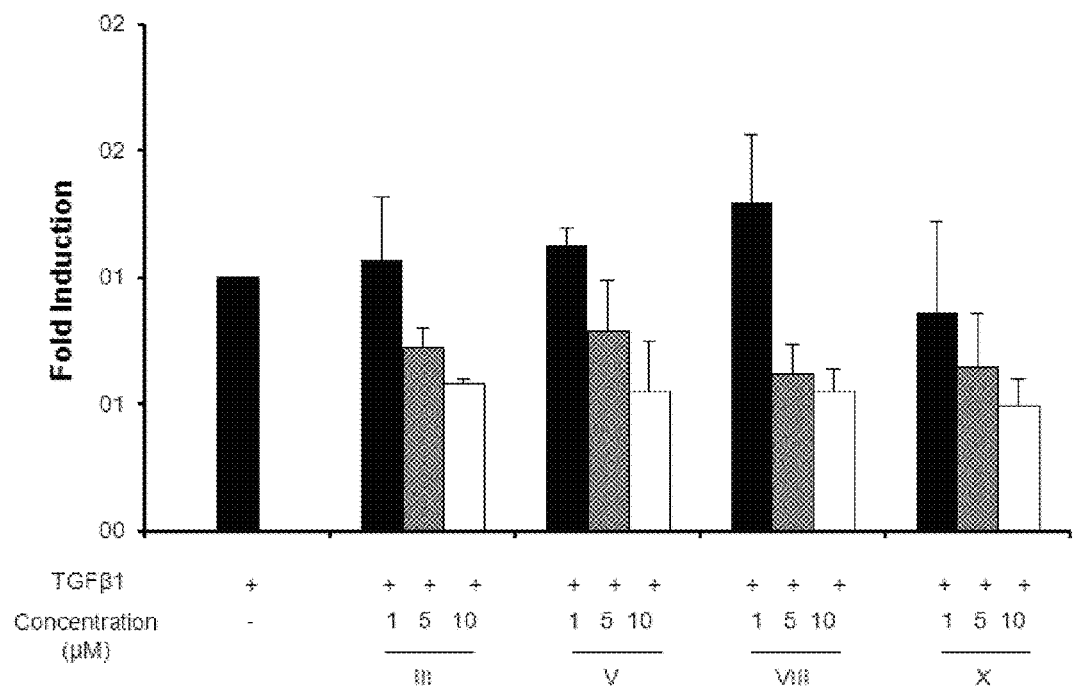

FIG. 8. Inhibition of TGFb-induced type II COLLAGEN

The production of collagen was carried out using the Sirius Red-Fast Green method, designed to quantify the amount of collagen and non-collagen proteins in cell pellets. The collagen production was determined at 540 nm and 605 nm in a Genesis 10 UV scanning spectrofluorometer (Thermo Fisher Scientific). To calculate the amounts of collagen, first, we corrected the OD 540 value by subtracting the contribution by Fast Green, which interfere in the absorbance at 540 nm. Fast Green contributes 29.1% of the OD 540 value. The Color equivalence is 37.8 for collagen and 2.04 for non-collagen proteins at OD 540 and 640, respectively.

$$\text{Collagen(pg/100 µl cell pellet)} = \{[OD\ 540-(OD\ 605 \times 0.291)]/37.8 \times 1000\} \times 10^6.$$

The experiments were repeated three times, and the results were expressed as a fold induction over untreated cells.

Figure 9:
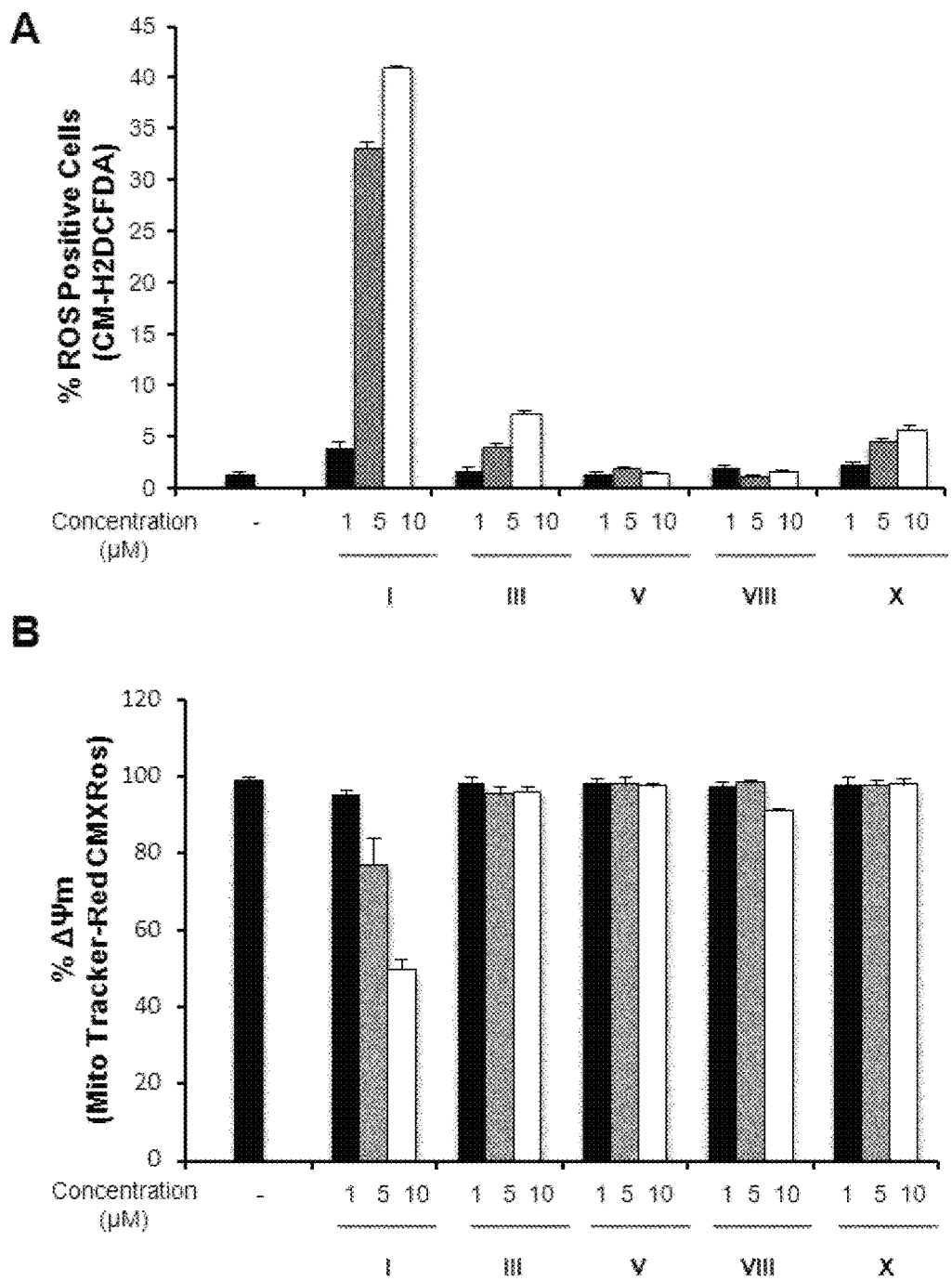

FIG. 9. Effect of CBD-Q derivatives on ROS generation and mitochondria transmembrane potential Jurkat cells were treated with increasing concentrations of VCE-004 (HU-311 or compound I) or compounds III, V, VII and X (as example of compound I derivatives) for 2 hours for the detection of mithocondrial membrane potential or during 6 hours for the detection of reactive oxygen species (ROS).

Fluorescent probes H2DCF-DA (20 nM, green fluorescence) and MitoTracker Red CMXR (MTR-CMXR) (50 nM) are used is used respectively to detect ROS and mitochondrial membrane potential (Molecular Probes, Eugene, Oreg., USA). After treatment the cells were washed twice with cold phosphate buffer saline (PBS) and incubated in PBS with for 20 min at 37° C., followed by analysis on a FACSCantoII flow cytometer.

EXAMPLES

The examples of the present invention described below aim to illustrate its preferred embodiments without limiting its scope of protection.

Example 1

Chemical Synthesis and NMR Analysis

A) Synthesis of CBD Quinone Derivatives Starting from CBD. Synthesis of Compounds II to X Synthesis of VCE-004 (also named HU-331 or compound I) from CBD was carried out by using tBuOK in toluene, at r.t., in the presence of air (Scheme 1). Synthesis of derivatives substituted at 3-position with alkylamines was easily accomplished by reacting VCE-004 with a large excess of amine, at r.t., in an air-opened reaction system.

Scheme 1

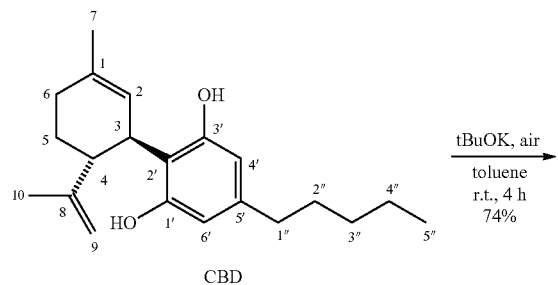

CBD

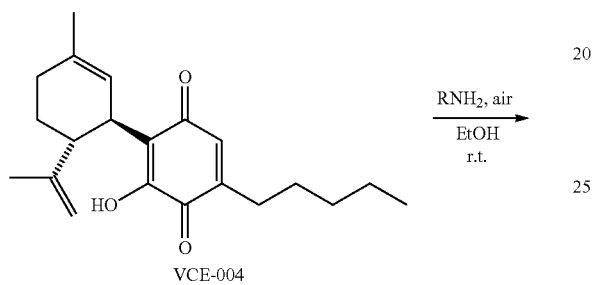

VCE-004

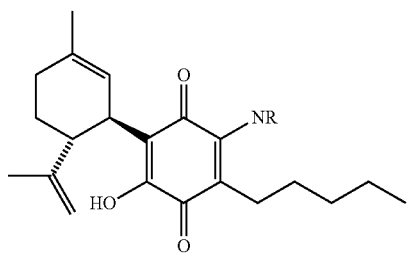

Flash chromatography purification furnished 90-95% pure product, which could be further increased up to 98% by means of HPLC purification. High conversion was achieved within several hours, to give spot-to-spot reactions. Solvent was evaporated, and the crude residue was purified by reverse phase chromatography, to give products with purities about 95%.

Preparation Compound I tBuOK (298 mg, 2.656 mmol) was added to a solution of CBD (302 mg, 0.960 mmol) in toluene (60 mL), to give a purple-colored solution. The reaction mixture was stirred at r.t., in an air-opened round bottom flask, and conversion was monitored by TLC analysis (eluent: 10% EtOAc/hexanes). After 4 h, the reaction mixture was washed with HCl (5% aqueous solution, 100 mL) and the aqueous layer was extracted with EtOAc (30 mL) (Scheme 2). Combined organic layers were dried over Na$_2$SO$_4$ (anhydrous), filtered and concentrated. The crude residue was flash chromatographed on SiO$_2$ (0®20% EtOAc/hexanes), to give 234 mg of VCE-004 (compound I) [brown-colored solid, yield: 74%].

Scheme 2

(Scheme 2 shows CBD converted to VCE-004 with tBuOK, air, toluene, r.t., 4 h, 74%)

Preparation Compound II (1'R,6'R)-3-(Ethylamine)-6-hydroxy-3'-methyl-4-pentyl-6'-(prop-1-en-2-yl)-[1,1'-bi(cyclohexane)]-2',3,6-triene-2,5-dione Ethylamine (1.0 mL, 70% solution in H$_2$O, 12.58 mmol) was added to a solution of VCE-004 (100 mg, 0.30 mmol) in EtOH (10 mL). The reaction mixture was stirred at r.t. for 2 h, and then worked by by pouring into water (50 mL), acidification to pH=2 with HCl (10% aqueous solution), and extraction with CH$_2$Cl$_2$ (30 mL) (Scheme 3). The organic layer was dried over Na$_2$SO$_4$ (anhydrous), filtered and concentrated. The crude residue was purified by reverse phase chromatography (30@100% CH$_3$CN/H$_2$O) to give 33 mg of (1'R,6'R)-3-(Ethylamine)-6-hydroxy-3'-methyl-4-pentyl-6'-(prop-1-en-2-yl)-[1,1'-bi(cyclohexane)]-2',3,6-triene-2,5-dione [purple-colored oil, yield: 29%].

$^1$H NMR (CDCl$_3$, 300 MHz) d ppm: 6.35 (bs, 1H), 5.13 (s, 1H), 4.57 (s, 2H), 3.61 (m, 1H), 3.52 (quin, J=13.2, 7.1 Hz, 2H), 2.73 (m, 1H), 2.48 (t, J=7.1 Hz, 2H), 2.26-1.80 (m, 2H), 1.68 (s, 3H), 1.63 (s, 3H), 1.46-1.24 (m, 9H), 0.89 (t, J=6.6 Hz, 3H).

Scheme 3

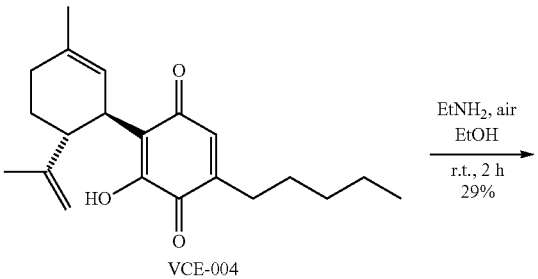

VCE-004

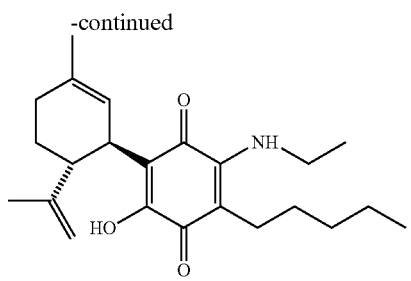

Preparation Compound III (1'R,6'R)-3-(Pentylamine)-6-Hydroxy-3'-methyl-4-pentyl-6'-(prop-1-en-2-yl)-[1,1'-bi(cyclohexane)]-2',3,6-triene-2,5-dione Amylamine (0.75 mL, 6.472 mmol) was added to a solution of VCE-004 (60 mg, 0.155 mmol) in EtOH (10 mL). The reaction mixture was stirred at r.t. for 18 h. It was poured into H$_2$O (50 mL), taken up to pH=2 with HCl (10% aqueous solution) and extracted with CH$_2$Cl$_2$ (30 mL) (Scheme 4). The organic layer was dried over Na$_2$SO$_4$ (anhydrous), filtered and concentrated. Crude residue was purified by reverse phase chromatography (30®100% CH$_3$CN/H$_2$O) to give 47 mg of (1'R,6'R)-3-(Pentylamine)-6-hydroxy-3 '-methyl-4-pentyl-6'-(prop-1-en-2-yl)-[1,1'-bi(cyclohexane)]-2',3,6-triene-2,5-dione [purple-colored solid, yield: 73%].

$^1$H NMR (CDCl$_3$, 300 MHz) d ppm: 6.43 (bs, 1H), 5.14 (s, 1H), 4.55 (s, 2H), 3.62 (m, 1H), 3.46 (c, J=6.6 Hz, 2H), 2.72 (m, 1H), 2.48 (t, J=7.7 Hz, 2H), 2.31-1.72 (m, 4H), 1.68 (s, 3H), 1.64 (s, 3H), 1.48-1.24 (m, 12H), 0.90 (m, 6H).

Scheme 4

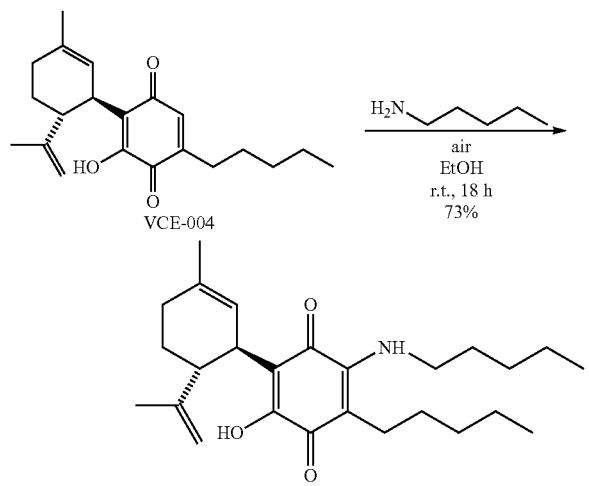

Preparation Compound IV (1'R,6'R)-3-(Isobutylamine)-6-Hydroxy-3'-methyl-4-pentyl-6'-(prop-1-en-2-yl)-[1,1'-bi(cyclohexane)]-2',3,6-triene-2,5-dione Isobutylamine (1.2 mL, 12.075 mmol) was added to a solution of VCE-004 (100 mg, 0.304 mmol) in EtOH (12 mL). The reaction mixture was stirred at r.t. for 22 h. It was poured into H$_2$O (50 mL), taken up to pH=2 with HCl (10% aqueous solution) and extracted with CH$_2$Cl$_2$ (30 mL) (Scheme 5). The organic layer was dried over Na$_2$SO$_4$ (anhydrous), filtered and concentrated. Crude residue was purified by reverse phase chromatography (30®100% CH$_3$CN/H$_2$O) to give 119 mg of (1'R,6'R)-3-(Isobutylamine)-6-hydroxy-3 '-methyl-4-pentyl-6'-(prop-1-en-2-yl)-[1,1'-bi(cyclohexane)]-2',3,6-triene-2,5-dione [purple-colored solid, yield: 97%].

$^1$H NMR (CDCl$_3$, 300 MHz) d ppm: 6.53 (bs, 1H), 5.15 (s, 1H), 4.56 (s, 2H), 3.62 (m, 1H), 3.27 (t, J=6.6 Hz, 2H), 2.73 (dt, J=12.0 Hz, 2.8 Hz, 1H), 2.47 (t, J=7.1 Hz, 2H), 2.27-1.72 (m, 4H), 1.68 (s, 3H), 1.64 (s, 3H), 1.47-1.29 (m, 7H), 1.00 (s, 3H), 0.97 (s, 3H), 0.89 (t, J=6.6 Hz, 3H).

Scheme 5

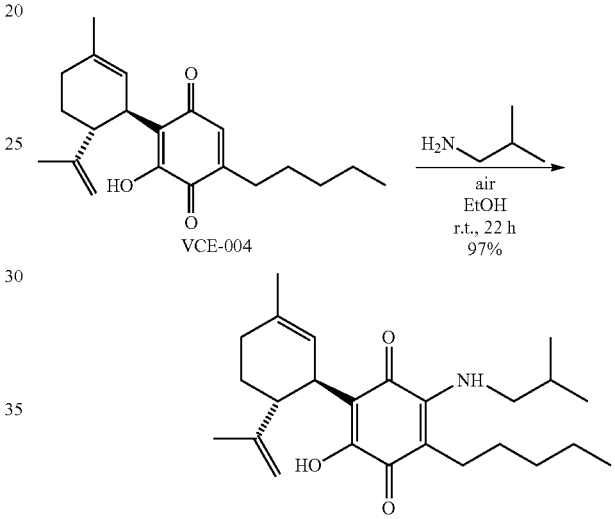

Preparation Compound V (1'R,6'R)-3-(Butylamine)-6-hydroxy-3'-methyl-4-pentyl-6'-(prop-1-en-2-yl)-[1,1'-bi(cyclohexane)]-2',3,6-triene-2,5-dione n-Butylamine (1.2 mL, 12.143 mmol) was added to a solution of VCE-004 (109 mg, 0.332 mmol) in EtOH (12 mL). The reaction mixture was stirred at r.t. for 18 h. It was poured into H$_2$O (50 mL), taken up to pH=2 with HCl (10% aqueous solution) and extracted with CH$_2$Cl$_2$ (30 mL) (Scheme 6). The organic layer was dried over Na$_2$SO$_4$ (anhydrous), filtered and concentrated. Crude residue was purified by reverse phase chromatography (30®100% CH$_3$CN/H$_2$O) to give 115 mg of (1'R,6'R)-3-(Butylamine)-6-hydroxy-3'-methyl-4-pentyl-6'-(prop-1-en-2-yl)-[1,1'-bi(cyclohexane)]-2',3,6-triene-2,5-dione [purple-colored solid, yield: 93%].

$^1$H NMR (CDCl$_3$, 300 MHz) d ppm: 6.44 (bs, 1H), 5.14 (s, 1H), 4.56 (s, 2H), 3.61 (m, 1H), 3.46 (q, J=6.6 Hz, 2H), 2.73 (m, 1H), 2.48 (t, J=7.1 Hz, 2H), 2.19 (m, 1H), 1.98 (m, 1H), 1.78-1.57 (m, 8H), 1.49-1.25 (m, 10H), 0.96 (t, J=7.1 Hz, 3H), 0.89 (m, 3H).

Scheme 6

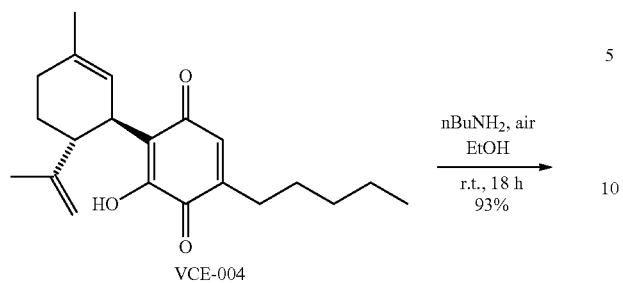

Preparation Compound VI (1'R,6'R)-3-(Methylamine)-6-Hydroxy-3'-methyl-4-pentyl-6'-(prop-1-en-2-yl)-[1,1'-bi(cyclohexane)]-2',3,6-triene-2,5-dione Methylamine (4.0 mL, 8 M solution in EtOH, 32.0 mmol) was added to a solution of VCE-004 (266 mg, 0.810 mmol) in EtOH (20 mL). The reaction mixture was stirred at r.t. for 7 h. It was poured into $H_2O$ (100 mL), taken up to pH=2 with HCl (10% aqueous solution) and extracted with $CH_2Cl_2$ (70 mL) (Scheme 7). The organic layer was dried over $Na_2SO_4$ (anhydrous), filtered and concentrated. Crude residue was purified by reverse phase chromatography (30®100% $CH_3CN/H_2O$) to give 114 mg of (1'R,6'R)-3-(Methylamine)-6-hydroxy-3'-methyl-4-pentyl-6'-(prop-1-en-2-yl)-[1,1'-bi(cyclohexane)]-2',3,6-triene-2,5-dione [purple-colored solid, yield: 39%].

$^1$H NMR (CDCl$_3$, 300 MHz) d ppm: 8.38 (bs, 1H), 6.54 (m, 1H), 5.12 (s, 1H), 4.56 (s, 2H), 3.63 (m, 1H), 3.19 (d, J=6.0 Hz, 3H), 2.71 (dt, J=11.5 Hz, 2.7 Hz, 1H), 2.54 (t, J=7.1 Hz, 2H), 2.28-1.71 (m, 3H), 1.67 (s, 3H), 1.63 (s, 3H), 1.51-1.25 (m, 6H), 0.89 (t, J=7.1 Hz, 3H).

Scheme 7

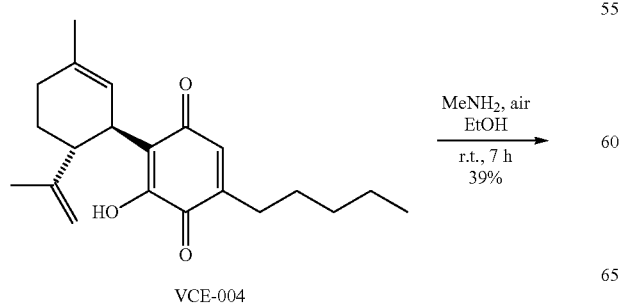

Preparation Compound VII (1'R,6'R)-3-(Isopropylamine)-6-Hydroxy-3'-methyl-4-pentyl-6'-(prop-1-en-2-yl)-[1,1'-bi(cyclohexane)]-2',3,6-triene-2,5-dione Isopropylamine (1.0 mL, 11.639 mmol) was added to a solution of VCE-004 (104 mg, 0.317 mmol) in EtOH (10 mL). The reaction mixture was stirred at r.t. for 22 h. It was poured into $H_2O$ (50 mL), taken up to pH=2 with HCl (10% aqueous solution) and extracted with $CH_2Cl_2$ (30 mL) (Scheme 8). The organic layer was dried over $Na_2SO_4$ (anhydrous), filtered and concentrated. Crude residue was purified by reverse phase chromatography (30@100% $CH_3CN/H_2O$) to give 92 mg of (1'R,6'R)-3-(Isopropylamino)-6-hydroxy-3'-methyl-4-pentyl-6'-(prop-1-en-2-yl)-[1,1'-bi(cyclohexane)]-2',3,6-triene-2,5-dione [purple-colored oil, yield: 75%].

$^1$H NMR (CDCl$_3$, 300 MHz) d ppm: 6.40 (m, 1H), 5.14 (s, 1H), 4.56 (s, 2H), 3.95 (m, 1H), 3.61 (m, 1H), 2.73 (m, 1H), 2.45 (t, J=6.6 Hz, 2H), 2.21 (m, 1H), 1.92 (m, 1H), 1.77 (m, 2H), 1.67 (s, 3H), 1.63 (s, 3H), 1.45-1.28 (m, 6H), 1.26 (s, 3H), 1.24 (s, 3H), 0.89 (t, J=7.1 Hz, 3H).

Scheme 8

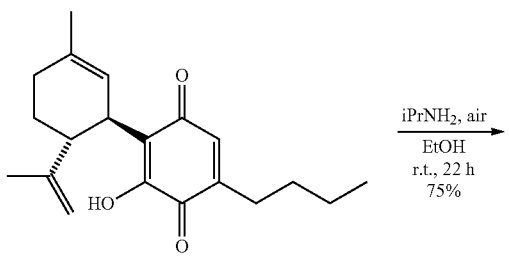

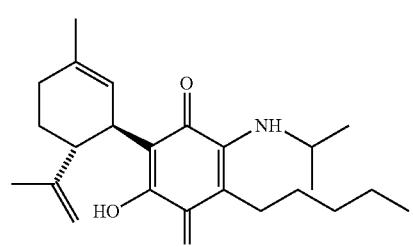

Preparation Compound VIII (1'R,6'R)-3-(Benzylamine)-6-hydroxy-3'-methyl-4-pentyl-6'-(prop-1-en-2-yl)-[1,1'-bi(cyclohexane)]-2',3,6-triene-2,5-dione Benzylamine (1.3 mL, 11.913 mmol) was added to a solution of VCE-004 (117 mg, 0.303 mmol) in EtOH (13 mL). The reaction mixture was stirred at r.t. for 18 h. It was poured into H$_2$O (50 mL), taken up to pH=2 with HCl (10% aqueous solution) and extracted with CH$_2$Cl$_2$ (30 mL). (Scheme 9). The organic layer was dried over Na$_2$SO$_4$ (anhydrous), filtered and concentrated. Crude residue was purified by reverse phase chromatography (30@100% CH$_3$CN/H$_2$O) to give 87 mg of (1'R,6'R)-3-(Benzylamine)-6-hydroxy-3'-methyl-4-pentyl-6'-(prop-1-en-2-yl)-[1,1'-bi(cyclohexane)]-2',3,6-triene-2,5-dione [purple-colored solid, yield: 66%].

$^1$H NMR (CDCl$_3$, 300 MHz) d ppm: 8.30 (bs, 1H), 7.44-7.26 (m, 5H), 6.64 (m, 1H), 5.15 (s, 1H), 4.65 (d, J=6.0 Hz, 2H), 4.59 (m, 2H), 3.64 (m, 1H), 2.73 (m, 1H), 2.47 (t, J=7.7 Hz, 2H), 2.30-1.76 (m, 4H), 1.68 (s, 3H), 1.64 (s, 3H), 1.54-1.23 (m, 6H), 0.88 (m, 3H)

$^1$H NMR (CDCl$_3$, 300 MHz) d ppm: 6.59 (m, 1H), 5.15 (s, 1H), 4.56 (s, 2H), 3.63 (m, 1H), 3.26 (d, J=5.5 Hz, 2H), 2.74 (dt, J=12.0 Hz, 3.3 Hz, 1H), 2.49 (t, J=7.1 Hz, 2H), 2.26-1.83 (m, 3H), 1.68 (s, 3H), 1.63 (s, 3H), 1.50-1.23 (m, 7H), 1.00 (s, 9H), 0.90 (t, J=6.6 Hz, 3H Scheme 10

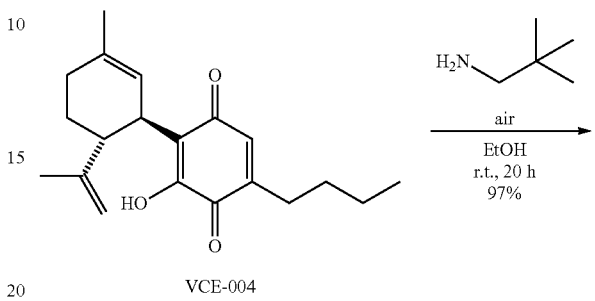

Scheme 9

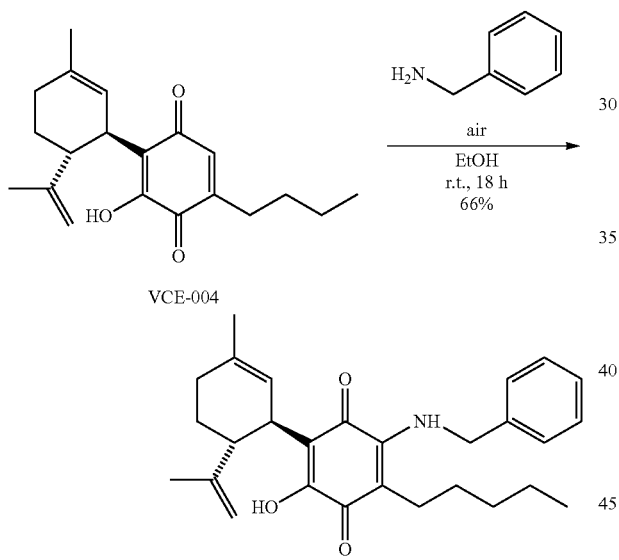

Preparation Compound IX (1'R,6'R)-3-(Neopentylamine)-6-Hydroxy-3'-methyl-4-pentyl-6'-(prop-1-en-2-yl)-[1,1'-bi(cyclohexane)]-2',3,6-triene-2,5-dione Neopentylamine (0.7 mL, 6.031 mmol) was added to a solution of VCE-004 (47 mg, 0.143 mmol) in EtOH (7 mL). The reaction mixture was stirred at r.t. for 20 h. It was poured into H$_2$O (50 mL), taken up to pH=2 with HCl (10% aqueous solution) and extracted with CH$_2$Cl$_2$ (30 mL) (Scheme 10). The organic layer was dried over Na$_2$SO$_4$ (anhydrous), filtered and concentrated. Crude residue was purified by reverse phase chromatography (30®100% CH$_3$CN/H$_2$O) to give 57 mg of (1'R,6'R)-3-(Neopentylamine)-6-hydroxy-3'-methyl-4-pentyl-6'-(prop-1-en-2-yl)-[1,1'-bi(cyclohexane)]-2',3,6-triene-2,5-dione [purple-colored oil, yield: 97%].

Preparation Compound X (1'R,6'R)-3-(Isopentylamine-6-Hydroxy)-3'-methyl-4-pentyl-6'-(prop-1-en-2-yl)-[1,1'-bi(cyclohexane)]-2',3,6-triene-2,5-dione Isopentylamine (1.5 mL, 12.735 mmol) was added to a solution of VCE-004 (101 mg, 0.307 mmol) in EtOH (15 mL). The reaction mixture was stirred at r.t. for 22 h. It was poured into H$_2$O (50 mL), taken up to pH=2 with HCl (10% aqueous solution) and extracted with CH$_2$Cl$_2$ (30 mL) (Scheme 11). The organic layer was dried over Na$_2$SO$_4$ (anhydrous), filtered and concentrated. Crude residue was purified by reverse phase chromatography (30®100% CH$_3$CN/H$_2$O) to give 125 mg of (1'R,6'R)-3-(Isopentylamine)-6-hydroxy-3 '-methyl-4-pentyl-6'-(prop-1-en-2-yl)-[1,1'-bi(cyclohe-xane)]-2',3,6-triene-2,5-dione [purple-colored oil, yield: 98%].

$^1$H NMR (CDCl$_3$, 300 MHz) d ppm: 6.38 (bs, 1H), 5.13 (s, 1H), 4.55 (s, 2H), 3.61 (m, 1H), 3.48 (q, J=6.0 Hz, 2H), 2.72 (m, 1H), 2.48 (t, J=7.1 Hz, 2H), 2.21 (m, 1H), 2.00-1.60 (m, 8H), 1.54 (q, J=7.1 Hz, 2H), 1.46-1.23 (m, 8H), 0.95 (s, 3H), 0.93 (s, 3H), 0.88 (t, J=6.6 Hz, 3H).

Scheme 11

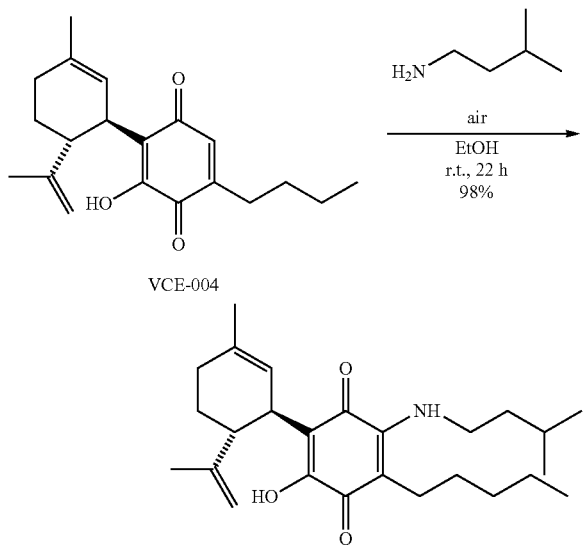

VCE-004

B) Synthesis of CBD Quinone Derivatives from Cannabidiol Acid CBDA. Synthesis of Compounds XI to XV

Synthesis of the Precursor of Compound XI

Methyl 4-hydroxy-5-((1R,6R)-3-methyl-6-(prop-1-en-2-yl)cyclohex-2-enyl)-3,6-dioxo-2-pentylcyclohexa-1,4-dienecarboxylate (CBDA-methyl ester)

Scheme 12

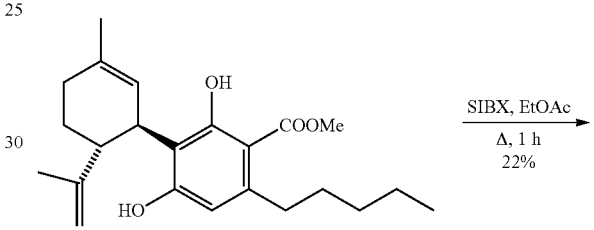

a) To a solution of Cannabidiol acid (CBDA) (180 mg, 0.40 mmol) in methanol (5 mL), dicyclohexylcarbodiimide (DCC) (163 mg, 1.6 mmol) and catalytic p-toluenesulfonic acid (ca. 5 mg) was added (Scheme 12). After stirring for 40 min., the reaction was worked up by evaporation. The residue was dissolved in toluene (ca 10 mL), and cooled (−18° C.) to precipitate the urea. After 1 h, the solution was filtered on a sintered glass filter, and the residue was purified by flash chromatography of RP C-18 silica gel to afford 140 mg of methyl 4-hydroxy-5-((1R,6R)-3-methyl-6-(prop-1-en-2-yl)cyclohex-2-enyl)-3,6-dioxo-2-pentylcyclohexa-1,4-dienecarboxylate [colorless foam, yield: 75%].

b) To a solution of Cannabidiol acid (CBDA) (200 mg, 0.54 mmol) in methanol (8 mL), trimethylsilyldiazomethane (3.0 mL, 2 M in hexanes) was added (Scheme 12). After stirring 5 min at room temperature, the reaction was worked up by evaporation. The product was sufficiently pure to be directly used in the oxidation step.

$^1$H NMR (CDCl$_3$, 300 MHz) δ ppm 11.97 (s, 1H), 6.40 (bs, 1H), 6.21 (s, 1H), 5.54 (bs, 1H), 4.51 (bs, 1H), 4.38 (bs, 1H), 3.90 (s, 3H), 2.77 (m, 2H), 1.81 (bs, 3H), 1.70 (bs, 3H), 0.89 (t, J=6.6 Hz, 3H).

Preparation of Compound XI

Methyl 4-hydroxy-5-((1R,6R)-3-methyl-6-(prop-1-en-2-yl)cyclohex-2-enyl)-3,6-dioxo-2-pentylcyclohexa-1,4-dienecarboxylate

Scheme 13

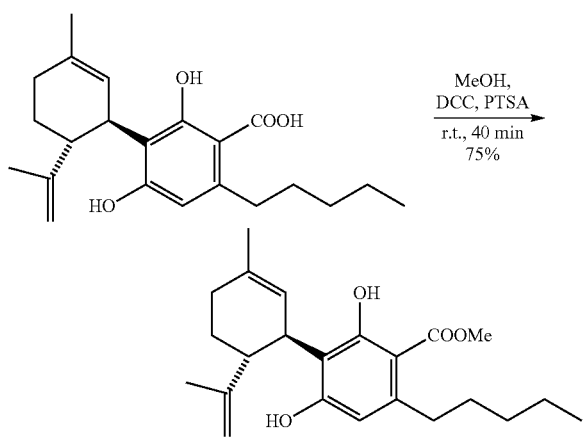

To a solution of 100 mg (0.27 mmol) of Methyl 4-hydroxy-5-((1R,6R)-3-methyl-6-(prop-1-en-2-yl)cyclohex-2-enyl)-3,6-dioxo-2-pentylcyclohexa-1,4-dienecarboxylate (CBDA-methyl ester) in 4 mL EtOAc, SIBX (460 mg, 0.77 mmol, 3 mol equiv.) was added, and the reaction was refluxed for 1 h (Scheme 13). After cooling and filtration over Celite, the filtrate was sequentially washed with 5% NaHCO$_3$ and brine. After drying (Na$_2$SO$_4$) and evaporation, the residue was purified by column chromatography on silica gel (petroleum ether-CH$_2$Cl$_2$ 8:5 as eluent) to afford 24 mg of compound XI [brown-colored solid, yield: 22%].

$^1$H NMR (CDCl$_3$, 300 MHz) δ ppm 7.00 (bs, 1H), 5.13 (bs, 1H), 4.57 (s, 1H), 4.53 (s, 1H), 3.89 (s, 3H), 3.73 (bd, J=7.0 Hz, 1H), 2.74 (td, J=9.1, 9.1, 1.5 Hz, 1H), 2.36 (t, J=7.5 Hz, 2H), 1.72 (bs, 3H), 1.64 (bs, 3H), 0.88 (t, J=6.6 Hz, 3H).

Synthesis of the Precursor of Compound XII

Phenethyl 2,4-dihydroxy-3-((1R,6R)-3-methyl-6-(prop-1-en-2-yl)cyclohex-2-enyl)-6-pentylbenzoate (CBDA-phenethyl ester)

Scheme 14

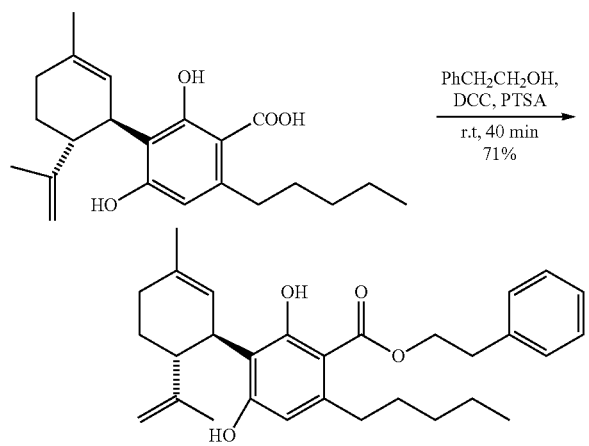

To a solution of cannabidiolic acid (CBDA) (2.15 g, 6.0 mmol) in CH$_2$Cl$_2$ (20 mL), phenethyl alcohol (0.860 mL) was added, followed by DCC (2.550 g, 12 mmol, 2 mol. equiv) and cat. PTSA (30 mg). After 1 h, the reaction was worked up by evaporation, and the residue was dissolved in toluene e cooled at −18° C. for 20 min to precipitate dicyclohexylurea. After filtration, the filtrate was evaporated, and the residue purified by flash chromatography on RP18 silica gel using a methanol-water gradient (from 6:4 to pure methanol) as eluant. 1.52 g (71%) of an oil were obtained.

$^1$H NMR (CDCl$_3$, 300 MHz) d ppm 12.0 (s, 1H), 7.35-7.24 m, 5H), 6.51 (bs, 1H), 6.21 (s, 1H), 5.55 (bs, 1H), 4.55 (t, J=7.5 Hz, 1H), 4.53 (bs, 1H), 4.38 (bs, 1H), 4.10 (bs, 1H), 3.10 (t, J=7.5 Hz, 2H), 2.70 (m, 2H), 1.79 (bs, 3H), 1.71 (bs, 3H), 0.88 (t, J=6.6 Hz, 3H).

Preparation of Compound XII

Phenethyl 4-hydroxy-5-((1R,6R)-3-methyl-6-(prop-1-en-2-yl)cyclohex-2-enyl)-3,6-dioxo-2-pentylcyclohexa-1,4-dienecarboxylate Scheme 15

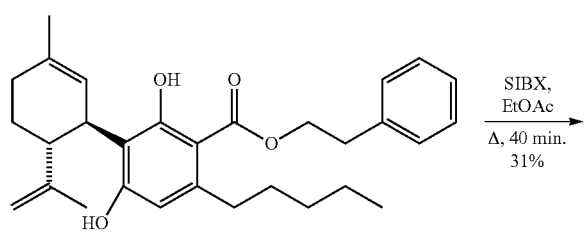

To a solution of 302 mg (0.65 mmol) of phenethyl 2,4-dihydroxy-3-((1R,6R)-3-methyl-6-(prop-1-en-2-yl)cyclohex-2-enyl)-6-pentylbenzoate in 4 mL EtOAc, SIBX (1.10 g, 39.1 mmol, 6 mol. equiv) was added, and the reaction was refluxed for 1 h (Scheme 15). After cooling and filtration over Celite, the filtrate was sequentially washed with 5% NaHCO$_3$ and brine. After drying (Na$_2$SO$_4$) and evaporation, the residue was purified by flash chromatography on RP-18 silica gel using a methanol-water gradient (from 6:4 to pure methanol) as eluant, to eventually afford 94 mg (31%) of compound XII.

$^1$H NMR (CDCl$_3$, 300 MHz) δ ppm 7.00 (bs, 1H), 5.14 (bs, 1H), 4.54 (s, 1H), 4.52 (s, 1H), 4.51 (t, J=7.5 Hz), 3.74 (bd, J=7.0 Hz, 1H), 3.02 (t, J=7.5 Hz, 2H), 2.75 (br t, J=9.1 1.5 Hz, 1H), 2.26 (t, J=7.5 Hz, 2H), 1.74 (bs, 3H), 1.67 (bs, 3H), 0.86 (t, J=6.6 Hz, 3H).

Synthesis of the Precursor of Compound XIII (E)-3,7-dimethylocta-2,6-dienyl2,4-dihydroxy-3-((1R,6R)-3-methyl-6-(prop-1-en-2 yl)cyclohex-2-enyl)-6-pentylbenzoate (CBDA-geranyl ester)

Scheme 16

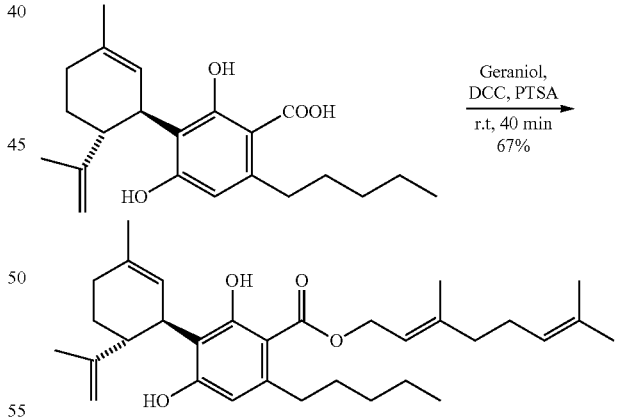

To a solution of cannabidiolic acid (CBDA) (300 mg, 0.84 mmol) in CH$_2$Cl$_2$ (4 mL), geraniol (0.18 mL. 10.1 mmol, 1.2 mol. equiv.) was added, followed by DCC (345 mg, 1.68 mmol, 2 mol. equiv) and cat. PTSA (30 mg). After 25 min, the reaction was worked up by evaporation, and the residue was dissolved in toluene e cooled at −18° C. for 20 min to precipitate dicyclohexylurea. After filtration, the filtrate was evaporated, and the residue purified by flash chromatography on gravity silica gel chromatography using petroleum ether-EtOAc 95:5 as eluanti. 200 mg (67%) of colorless oil were obtained.

$^1$H NMR (CDCl$_3$, 300 MHz) d ppm 12.1 (s, 1H), 6.48 (bs, 1H), 6.20 (s, 1H), 5.54 (bs, 1H), 5.45 (brt, J=6.7 Hz, 1H), 5.08 ((br s, 1H), 4.81 (d, J=6.7 Hz, 2H), 4.51 (bs, 1H), 4.38 (bs, 1H), 4.08 (bs, 1H), 2.74 (m, 2H), 1.78 (bs, 3H), 1.75 (bs, 3H), 1.71 (bs, 3H), 1.67 (bs, 3H), 0.88 (t, J=6.6 Hz, 3H).

Preparation of Compound XIII (E)-3,7-dimethylocta-2,6-dienyl-4-hydroxy-5-((1R, 6R)-3-methyl-6-(prop-1-en-2-yl)cyclohex-2-enyl)-3, 6-dioxo-2-pentylcyclohexa-1,4-dienecarboxylate Scheme 17

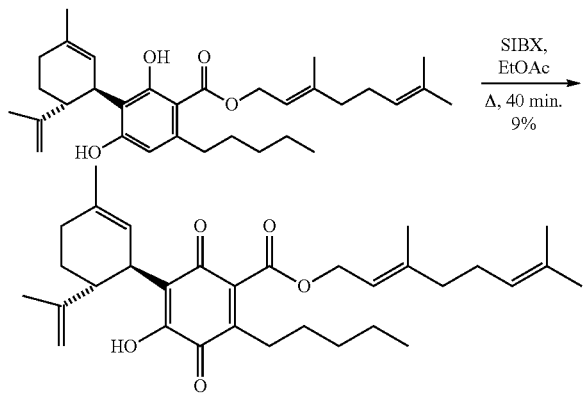

To a solution of 200 mg (0.40 mmol) of (E)-3,7-dimethylocta-2,6-dienyl2,4-dihydroxy-3-((1R,6R)-3-methyl-6-(prop-1-en-2yl)cyclohex-2-enyl)-6-pentyl-benzoate in 4 mL EtOAc, SIBX (680 mg, 2.4 mmol, 6 mol. equiv) was added, and the reaction was refluxed for 40 min (Scheme 17). After cooling and filtration over Celite, the filtrate was sequentially washed with 5% NaHCO$_3$ and brine. After drying (Na$_2$SO$_4$) and evaporation, the residue was purified by flash chromatography on RP-18 silica gel, using using a methanol-water gradient (from 6:4 to pure methanol) as eluant, eventually affording 18 mg (9%) of compound XIII.

$^1$H NMR (CDCl$_3$, 300 MHz) δ ppm 6.99 (bs, 1H), 5.38 (bt, J=6.8 Hz, 1H), 5.12 (bs, 1H), 5.07 (bs, 1H), 4.81 (bs, 1H), 4.80 (bs, 1H), 4.56 (bs, 1H), 3.97 (d, J=6.8 Hz, 2H), 2.73 (m, 1H), 2.37 (m, 2H), 1.73 (bs, 3H), 1.70 (bs, 3H), 1.67 (bs, 3H), 1.62 (bs, 3H), 0.86 (t, J=6.9 Hz, 3H).

Synthesis of the Precursor of Compound XIV (1S, 2S, 4R)-1,7,7-trimethylbicyclo[2.2.1]heptan-2-yl-2,4-dihydroxy-3-((1R,6R)-3-methyl-6-(prop-1-en-2-yl)cyclohex-2-enyl)-6-pentylbenzoate (CBDA bornyl ester)

Scheme 18

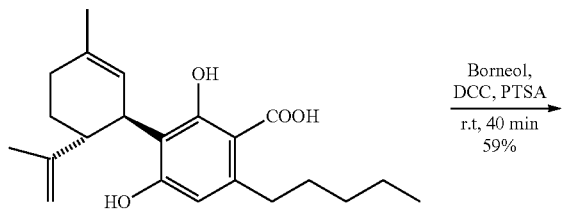

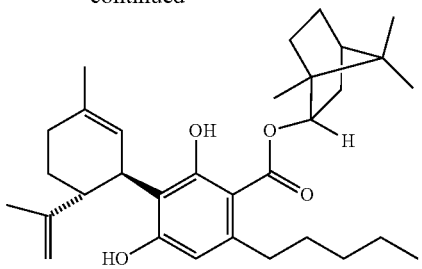

To a solution of cannabidiolic acid (CBDA) (302 mg, 0.84 mmol) in CH$_2$Cl$_2$ (4 mL), (−) (S)-borneol (157 mg, 1.2 mol. equiv.) was added, followed by DCC (350 mg, 2 mol. equiv) and cat. PTSA (30 mg). After 40 min, the reaction was worked up by evaporation, and the residue was dissolved in toluene e cooled at −18° C. for 20 min to precipitate dicyclohexylurea. After filtration, the filtrate was evaporated, and the residue purified by flash chromatography on RP18-silica gel using a methanol-water gradient (from 6:4 to pure methanol) as eluant. 178 mg (59%) of colorless oil were eventually obtained.

$^1$H NMR (CDCl$_3$, 300 MHz) d ppm 12.2 (s, 1H), 6.48 (bs, 1H), 6.23 (s, 1H), 5.54 (bs, 1H), 5.54 (bs, 1H), 5.19 ((br s, 1H), 4.52 (bs, 1H), 4.40 (bs, 1H), 4.12 (bs, 1H), 2.91 (m, 2H), 1.80 (bs, 3H), 1.71 (bs, 3H), 0.96 (s, 3H), 0.89 (s, 6H), 0.88 (t, J=6.6 Hz, 3H).

Preparation of Compound XIV ((1S, 2S, 4R)—)-1,7,7-trimethylbicyclo[2.2.1]heptan-2-yl-4-hydroxy-5-((1R,6R)-3-methyl-6-(prop-1-en-2-yl)cyclohex-2-enyl)-3,6-dioxo-2-pentylcyclohexa-1,4-dienecarboxylate Scheme 19

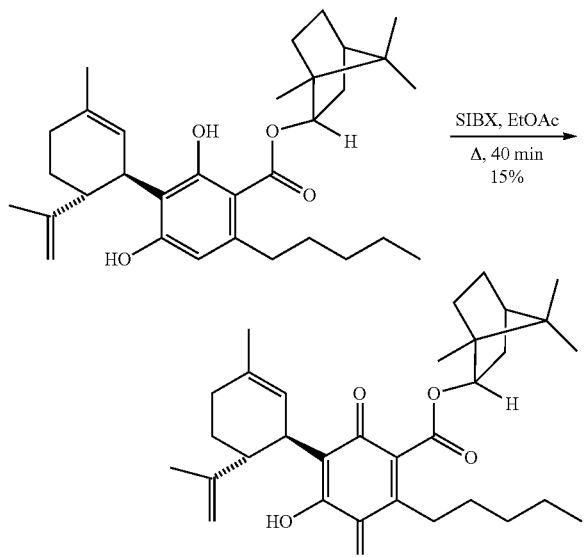

To a solution of 170 mg (0.34 mmol) of (1S, 2S, 4R)-1, 7,7-trimethyl-bicyclo [2.2.1]heptan-2-yl-2,4-dihydroxy-3-((1R,6R)-3-methyl-6-(prop-1-en-2-yl)cyclohex-2-enyl)-6-pentylbenzoate in 4 mL EtOAc, SIBX (578 mg, 2.1 mmol, 6 mol. equiv) was added, and the reaction was refluxed for 40 min (Scheme 19). After cooling and filtration over Celite, the filtrate was sequentially washed with 5% NaHCO$_3$ and brine. After drying (Na$_2$SO$_4$) and evaporation, the residue was purified by gravity column chromatography on silica gel, using using petroleum ether-EtOAc 98:2 as eluant, affording 25 mg (15%) of compound XIV.

$^1$H NMR (CDCl$_3$, 300 MHz) δ ppm 6.98 (bs, 1H), 5.16 (bs, 1H), 5.10 (bd, J=10 Hz, 1H), 4.58 (bs, 1H), 4.56 (bs, 1H), 3.75 (bd, J=6.8 Hz, 1H), 2.73 (m, 1H), 2.37 (m, 2H), 1.61 (bs, 3H), 0.92 (s, 3H), 0.90 (s, 3H), 0.88 (s, 3H), 0.86 (t, J=6.9, 3H).

Synthesis of the Precursor of Compound XV (1R,2R,4R)-1,5,5-Trimethylbicyclo[2.2.1]heptan-2-yl-2,4-dihydroxy-3-((1R,6R)-3-methyl-6-(prop-1-en-2-yl)cyclohex-2-enyl)-6-pentylbenzoate (CBDA fenchyl ester)

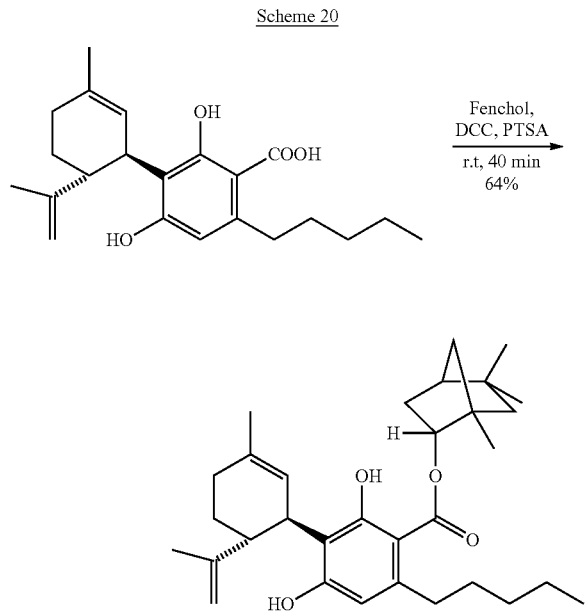

To a solution of cannabidiol acid (CBDA) (550 mg, 1.54 mmol) in CH$_2$Cl$_2$ (4 mL), (+) (R)-fenchol (284 mg, 1.2 mol. equiv.) was added, followed by DCC (634 mg, 2 mol. equiv) and cat. PTSA (30 mg). After 40 min, the reaction was worked up by evaporation, and the residue was dissolved in toluene e cooled at −18° C. for 20 min to precipitate dicyclohexylurea. After filtration, the filtrate was evaporated, and the residue purified by gravity column chromatography on silica gel to afford 350 mg (64%) of colorless oil.

$^1$H NMR (CDCl$_3$, 300 MHz) δ ppm 12.34 (s, 1H), 6.50 (bs, 1H), 6.24 (s, 1H), 5.57 (bs, 1H), 4.64 (bs, 1H), 4.52 (bs, 1H), 4.39 (bs, 1H), 4.10 (bs, 1H), 2.97 (m, 2H), 1.71 (bs, 3H), 1.20 (s, 3H), 1.14 (s, 3H), 0.96 (s, 3H), 0.89 (s, 6H), 0.89 (t, J=6.6 Hz, 3H), 0.79 (s, 3H).

Preparation of Compound XV (1R,2R,4R)-1,5,5-trimethylbicyclo[2.2.1]heptan-2-yl 4-hydroxy-5-((1R,6R)-3-methyl-6-(prop-1-en-2-yl)cyclohex-2-enyl)-3,6-dioxo-2-pentylcyclohexa-1,4-dienecarboxylate

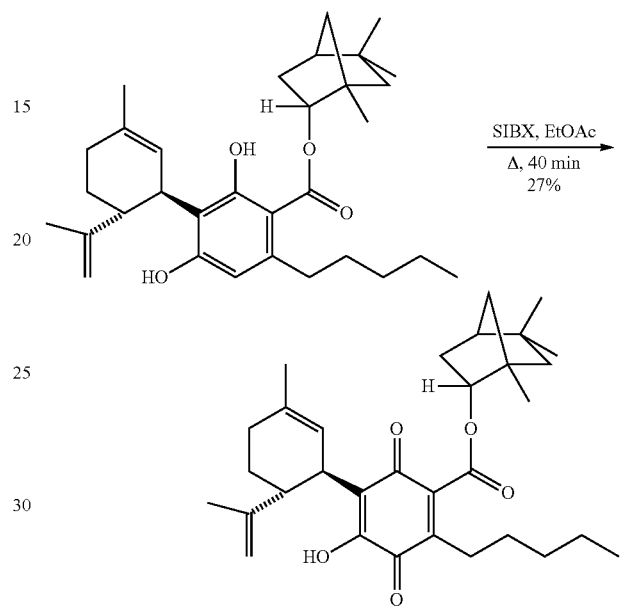

To a solution of 300 mg (0.61 mmol) of (1R, 2R, 4R)-1,5,5-trimethylbicyclo[2.2.1]-heptan-2-yl-2,4-dihydroxy-3-((1R,6R)-3-methyl-6-(prop-1-en-2-yl)cyclohex-2-enyl)-6-pentylbenzoate in 4 mL EtOAc, SIBX (1.019 g, 6 mol. equiv) was added, and the reaction was refluxed for 40 min (Scheme 21). After cooling and filtration over Celite, the filtrate was sequentially washed with 5% NaHCO$_3$ and brine. After drying (Na$_2$SO$_4$) and evaporation, the residue was purified by gravity column chromatography on silica gel, using using petroleum ether-EtOAc 98:2 as eluant, affording 81 mg (27%) of compound XV.

$^1$H NMR (CDCl$_3$, 300 MHz) δ ppm 6.98 (bs, 1H), 5.16 (bs, 1H), 5.10 (bd, J=10 Hz, 1H), 4.60 (bs, 1H), 4.57 (bs, 1H), 4.55 (bs, 1H), 3.73 (bd, J=10 Hz, 1H), 2.73 (m, 1H), 2.38 (m, 2H), 1.67 (bs, 3H), 1.15 (s, 3H), 1.10 (s, 3H), 0.86 (s, 3H), 0.86 (t, J=6.9, 3H).

In Vitro Assays

Example 2

PPARg Agonistic Activity

To investigate the biological activities of the novel compounds we performed PPARg transactivation assays in HEK-293 cells and in NIH-3T3 fibroblasts cells.

Figure 1A:
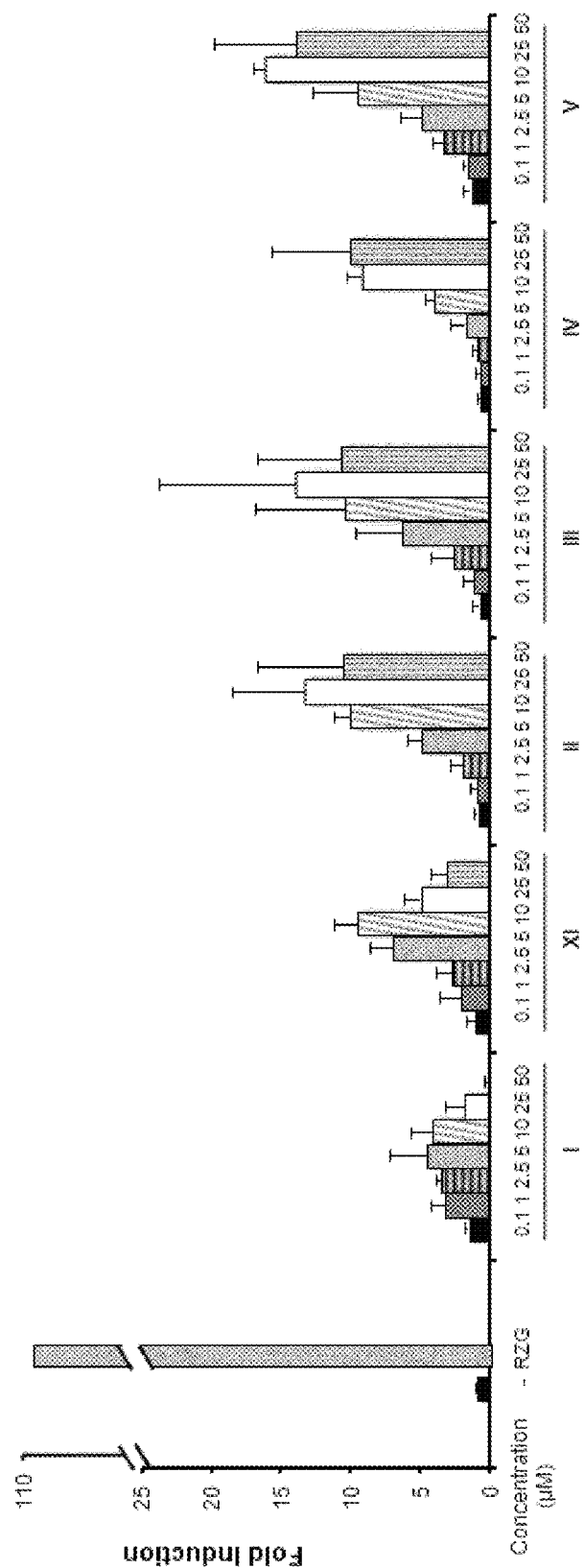
Figure 1B:
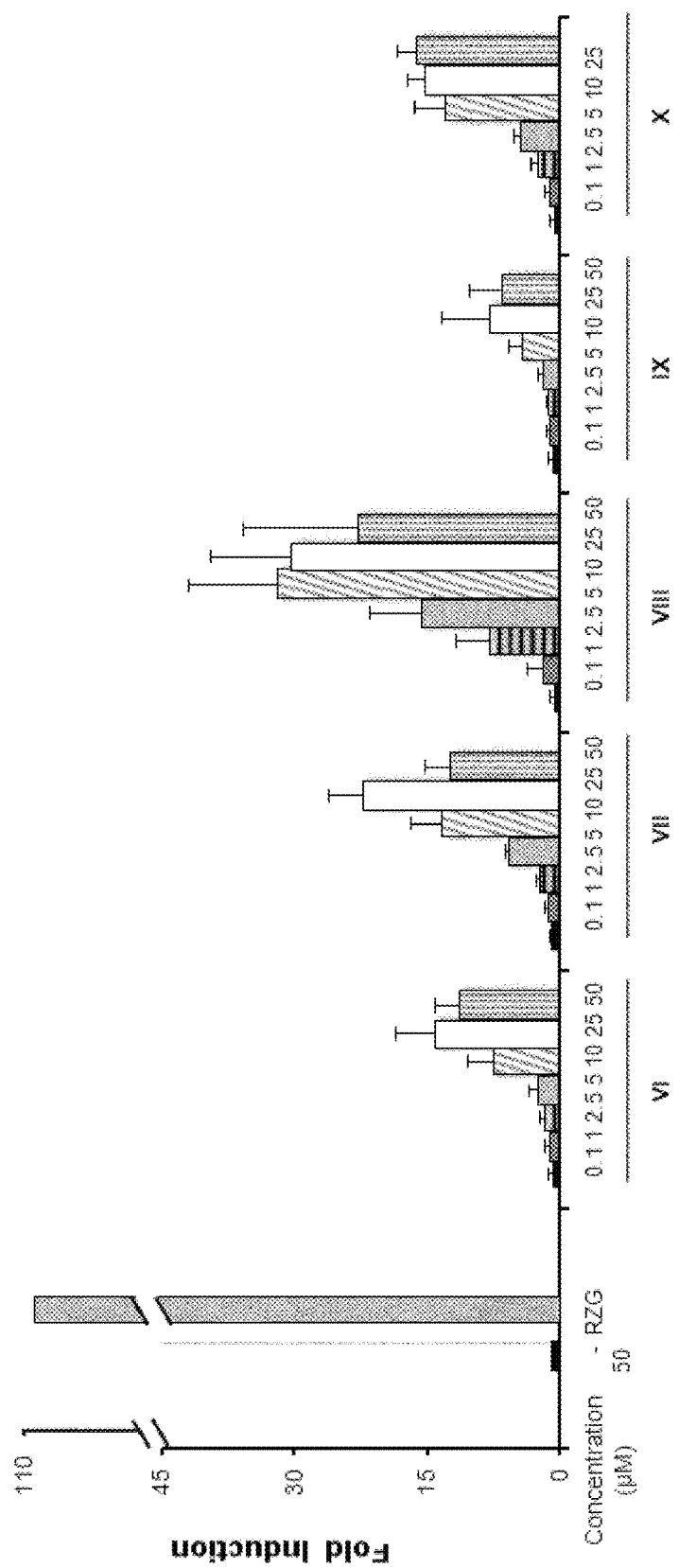
Figure 1C:
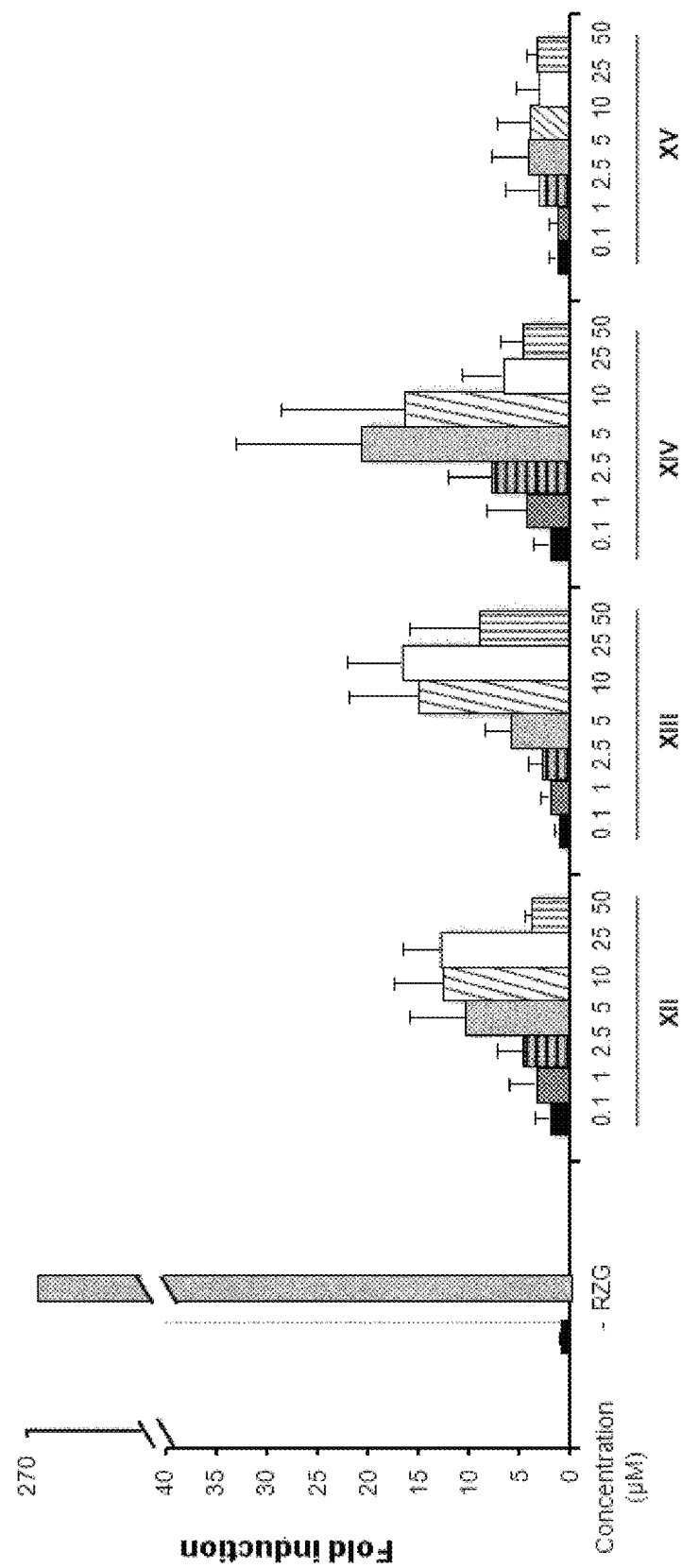

HEK293T cells and human primary fibroblasts cells were maintained at 37° C. in a humidified atmosphere containing 5% CO$_2$ in DMEM supplemented with 10% fetal calf serum (FBS), and 1% (v/v) penicillin/streptomycin. Rosiglitazone was purchased from Cayman Chemical Company (Ann Arbor, Mich., USA). All other reagents were from Sigma Co (St Louis, Mo., USA). HEK293T cells ($2\times10^3$/well) (FIGS. 1A, 1B and 1C) or NIH-3T3 cells ($5\times10^3$/well) (FIG. 2) were seeded in BD Falcon™ White with Clear Bottom 96-well Microtest™ Optilux™ Plate for 24 hours. Afterwards, cells were transiently co-transfected with the expression vector GAL4-PPARγ and the luciferase reporter vector GAL4-luc using Roti©-Fect (Carl Roth, Karlsruhe, Germany) following the manufacturer's instructions. Twenty-four h post-transfection, cells were pretreated with increasing doses of the compounds for 6 hours. Then, the cells were lysed in 25 mM Tris-phosphate pH 7.8, 8 mM $MgCl_2$, 1 mM DTT, 1% Triton X-100, and 7% glycerol. Luciferase activity was measured in the cell lysate using a TriStar LB 941 multimode microplate reader (Berthold) and following the instructions of the Luciferase Assay Kit (Promega, Madison, Wis., USA). Protein concentration was measured by the Bradford assay (Bio-Rad, Richmond, Calif., USA). The background obtained with the lysis buffer was subtracted in each experimental value and the specific transactivation expressed as a fold induction over untreated cells. All the experiments were repeated at least three times. The plasmids used were Gal4-hPPARgamma (plasmid name: pCMV-BD-hPPARg, Sinal Laboratory, Dept. of Pharmacology, Dalhousie University) and Gal4 luc reporter plasmid that includes five Gal4 DNA binding sites fused to the luciferase gene. The above assay is illustrated by FIGS. 1 (A, B and C) and FIG. 2 which shows the effect of VCE-004 (compound I) and analogues on PPARg activity by means of a transactivation assay performed in cells transiently over expressing PPARg in combination with a luciferase reporter gene (PPARg-GAL4/GAL4-LUC) and treated with the compounds for 6 hours. Data are given as means with deviation standard error bars of three replicates. A significant increase in luciferase activity was seen with quinone derivates as compared with untreated cells. This result confirms that compounds II to XIV are significantly more potent than compound VCE-004 (compound I) to activate PPARg at the concentrations of 5 to 50 µM. Compounds II to X increase PPARg transactivation in a concentration dependent manner, being II, III, IV, V, VII and VIII the most active compounds. In addition higher concentrations (10, 25 and 50 µM) of these compounds are particularly potent to activate PPARg compared to VCE-004 (compound I). RZG, a full PPARg agonist, increased more than 100 times the activity of PPARg at the concentration of 1 µM. In contrast the maximal induction of PPARg activity induced by 1 µM concentration of the compounds described in the present invention was never higher than 5 times indicating that these novel compounds are PPARg modulator and not PPARg full agonists.

Example 3

Cannabidiol-Quinone Derivatives and Rosiglitazone Bind to the Same Site in the PPARg Protein (A) HEK293T cells were maintained at 37° C. in a humidified atmosphere containing 5% $CO_2$ in DMEM supplemented with 10% fetal calf serum (FBS), and 1% (v/v) penicillin/streptomycin. Rosiglitazone was purchased from Cayman Chemical Company (Ann Arbor, Mich., USA). HEK293T cells ($2\times10^3$/well) (FIG. 3A) were seeded in BD Falcon™ White with Clear Bottom 96-well Microtest™ Optilux™ Plate for 24 hours. Afterwards, cells were transiently co-transfected with the expression vector GAL4-PPARγ and the luciferase reporter vector GAL4-luc using Roti©-Fect (Carl Roth, Karlsruhe, Germany) following the manufacturer's instructions. Twenty-four h post-transfection, cells were pretreated with increasing doses of the compounds for 30 min and then stimulated with RSZ (1 µM) for 6 hours. The transcriptional activity of PPARg was measured as in example 2, ratifying that those compounds III, V, VIII, X, and XIII are being able to able to decrease the RSZ-induced PPARg transactivation thus suggesting that compounds III, V, VIII, X, and XIII and RSZ may bind to the same binding site on PPARg.

(B) Binding features of compound VIII (as an example) to PPARg were calculated by virtual docking, using the AutoDock software and setting the Vina algorithm as calculation system. Search space was set to find binding points all around the molecular surface. To ensure the efficiency of the method docking features for the standard PPARg ligand RSZ were also calculated in order to use these results as control. AutoDock reported 10 stable conformations for each ligand (RSZ and Compound VIII). Six of these conformations for both RSZ and compound VIII matched the RSZ binding site previously reported [Liberato et al. 2012]. Residues Y473, H323, 1326, S289 and H449 in PPARg were established as anchoring positions and are part of a group of ten aminoacids with a close spatial location that form a binding site for PPARg ligands [Nolte et al. 1998], [Itot et al. 2008], [Li et al. 2008]. The RSZ binding site showed greater thermodynamic stability for compound VIII than for RSZ (FIG. 3B), suggesting a higher affinity on the former compound to this receptor. In fact, highest affinity compound VIII conformation showed a binding affinity of −8.0 KCal/mol, whereas RSZ best conformation showed −6.9 Kcal/mol. Nevertheless, only two of the 10 RSZ binding residues, 1341 and R288, in PPARg are likely interacting with compound VIII. Overall, these results suggest that compound VIII might bind to PPARg more strongly than RSZ in a closely related binding site, but with a different ligand-receptor interaction pattern, leading to different conformational effect on the receptor. Furthermore, blocking of 1341 and R288 would be enough to avoid the entry of RSZ, therefore decreasing the effect of this drug.

Example 4

Cytotoxicity Assays

Electrophilic quinones induce cytotoxicity and activate the Nrf2 pathway, a cellular sensor of reactive oxygen species generation. In FIG. 4 it is analyzed the induced cell death in three different types of cells N2a (A), HT22 (B) and MO3.13 (C) by compounds VCE-004 (compound I) and compounds II to XV.

Three cell lines, MO3.13, N2A and HT22 cells were maintained at 37° C. in a humidified atmosphere containing 5% $CO_2$ in DMEM supplemented with 10% fetal calf serum (FBS), and 1% (v/v) penicillin/streptomycin. N2A, HT22 and MO3.13 cell viability was determined by the MTT assay. Briefly, cells were seeded at a density of $10^4$ cells/well in 96-well plates, 200 µl cell suspension per well, and cultured for 24 hours. Cells were then incubated with several concentrations of the compounds for 24 hours. After that, 100 µl of MTT (5 mg/ml) from a mixture solution of MTT:DMEM (1:2) was added to each well, and cells were incubated for 4 h at 37° C. in darkness. Then the reaction was stopped, supernatant removed and 100 µl of DMSO added to each well and incubated for 10 minutes in gentle shaking. Finally the absorbance was measured at 550 nm using a TriStar LB 941 (Berthold Technologies, GmbH & Co. KG). Control cells were set as 100% and data were referred to that value. The cell lines N2a (FIG. 4A), HT22

(FIG. 4B) and MO3.13 (FIG. 4C) cells were incubated for 24 h with the indicated doses of compounds VCE-004 (compound I) and compounds II to XV, and cell viability was quantified by MTT assay. Results are shown as mean±S.D. from at least three independent experiments, and expressed as percentage of cell viability against the control sample (−). Control was set as 100% and data were referred to that value. The results demonstrate that the cytotoxic activity associated to VCE-004 (compound I) correlated with its ability to induce Nrf2 activation. In the same sense, the lack of cytotoxic activity described in the present invention for compounds II to XV derivatives in position 3' of VCE-004, is correlated with their inability to activate Nrf2.

Example 5

Nrf2 Transcriptional Activity

To study the activity of the compounds on the Nrf2 pathway we generated the HaCaT-ARE-Luc cell line. Nqo1 ARE-Luc reporter plasmid and pPGK-Puro plasmid were co-transfected into HaCat cells using Lipofectamine© 2000 transfection reagent (Life Technologies, Carlsbad, Ca, USA). Stable transformants were selected and maintained in RPMI 1640 containing 10% FBS, 1% penicillin-streptomycin and 10 μl/ml puromycin. HaCaT-ARE-Luc cells were incubated for 6 h with VCE-004 (compound I) and with compounds II to VIII (A) or with compounds IX to XV (B) at the indicated concentrations, and protein lysates were prepared and analysed for luciferase activity as described in example 1. The prooxidant tert-Butylhydroquinone (tBHQ) at 20 μM was used as positive control. Fold activation level was calculated, taking the control sample (−) as reference (FIGS. 5A and 5B). Data are expressed as mean±S.D. from at least three independent experiments. The results ratify that the reactive electrophilic activity associated to VCE-004 (compound I) is missing in all the compounds (derivatives in position 4) described in the present invention.

Example 6

Neuroprotection Assays

Activation of the nuclear receptor PPARg plays an important role in neuroprotection and it is known that PPARg agonists prevent glutamate-induced cytotoxicity in neuronal cells.

Cultured N2a cells were pre-incubated with the compounds I to VIII (FIG. 6A) and IX to XV (FIG. 6B) at the indicated concentrations for 1 h and then treated with 5 mM glutamate to induce excitotoxicity during 24 h. Cytotoxicity was determined by the MTT method as described in example 4. Results are shown as mean±S.D. from at least three independent experiments, and expressed as percentage of cell viability against the control sample (−). Control was set as 100% and data were referred to that value.

Those results show remarkable differences between compound I and compounds II to XV, which are PPARg modulators and also protect neuronal cells from glutamate-induced cell death.

Example 7

Effect of CBD-Quinone Derivatives on Collagen Gene Transcription

PPARg ligands have been reported to exert anti-fibrotic effects and TGFb signaling blockage by PPARg activation leads to decreased collagen production in fibroblasts.

Cultured NIH-3T3 fibroblast cells were transiently transfected with the plasmid COL1A2-Luc plasmid that contains sequences from −353 to +58 bp of the human COL1A2 promoter fused to the luciferase reporter gene. Twenty-four hour later the cells were incubated with compounds III, V, VIII and X (as examples) for 30 min and treated with TGFb (50 ng/ml) for 6 h. Protein lysates were prepared and analyzed for luciferase activity. It is shown that compounds III, V, VIII and X clearly inhibited TGFb-induced collagen type I gene transcription (FIG. 7).

Example 8

Effect of CBD-Quinone Derivatives on Collagen Production

The production of collagen was carried out using the Sirius Red-Fast Green method, designed to quantify the amount of collagen and non-collagen proteins in cell pellets. NIH-3T3 cells were seeded at a density of $5 \times 10^4$/well in 24 well plates and they were incubated overnight at 37° C. to allow cell attachment. Next, cells were pre-incubated 1 hour with the indicated concentrations of compounds III, V, VIII and X and TGFb (50 ng/ml) during 24 hours. After the treatment, the cell pellets were extracted overnight at 4° C. with 100 μl of 0.5M acetic acid. Then, 1 ml of the dye solution (0.1% Sirius Red and 0.1% Fast Green dissolved in saturated picric acid) was added to the cell pellets and mixed gently at room temperature for 30 minutes. Next, samples were centrifuged at 10,000 g for 5 minutes to pellet the collagen. The supernatants were carefully removed without disturbing the pellet and 1 ml of 0.1 M hydrochloric acid was added to each tube to remove unbound dye. Samples were centrifuged at 10,000 g for 5 minutes and 1 ml of 0.5 M sodium hydroxide was added to each tube and vortex vigorously to release the bound dye. Samples were centrifuged at 2500 g for 5 minutes to re-pellet any cell debris.

The collagen production was determined and the results were expressed as a fold induction over untreated cells. It is shown that compounds III, V, VIII and X clearly inhibited TGFb-induced collagen production in fibroblasts (FIG. 8). The cytotoxicity associated to VCE-004 (HU-331) did not allow to investigate the effect of this compound on TGFb-induced collagen production.

Example 9

Effects of VCE-004 and CDB-Quinone Derivatives on Reactive Oxygen Species (ROS) Production and on Mitochondria Transmembrane Potential Mitochondrial membrane potential is critical for maintaining the physiological function of the respiratory chain to generate ATP. A significant loss of mitochondrial membrane potential renders cells depleted of energy with subsequent death. Therefore, the ability to determine mitochondrial membrane potential and ROS can provide important clues about the physiological status of the cell and the function of the mitochondria in response to electrophilic and reactive molecules.

In FIG. 5 we showed that VCE-004 (compound I) is a reactive compound that activates the Nrf2 pathway. To further confirm the effect on the intracellular ROS production and on the disruption of mitochondrial membrane potential, we analyse HU-311 and the compounds of the present invention directly.

Jurkat cells were grown at 37° C. and 5% $CO_2$ in supplemented RPMI 1640 medium containing 10% heat-inactivated FCS, 2 mM glutamine and antibiotics. To evaluate the mitochondrial transmembrane potential and the reactive oxygen species (ROS) generation, the cells ($5\times10^5$/ml) were treated with increasing concentrations of VCE-004 (compound I) or with compounds III, V, VII and X (as examples of compound I derivatives) either for 2 hours for the detection of mitochondrial membrane potential or during 6 hours for the detection of ROS. After treatment the cells were washed twice with cold phosphate buffer saline (PBS) and incubated in PBS with the fluorescent probes H2DCF-DA (green fluorescence) (20 nM) to detect ROS and MitoTracker Red CMXR (MTR-CMXR) (50 nM) to detect mitochondrial membrane potential (Molecular Probes, Eugene, Oreg., USA) for 20 min at 37° C., followed by analysis on a FACSCantoII flow cytometer. We found that VCE-004 (compound I) induces a clear increase in the levels of intracellular ROS and a disruption of mitochondrial membrane potential. In contrast compounds III, V, VII and X were not reactive (increase ROS levels) and did not induce a loss in the mitochondrial membrane potential.

In FIG. 9A is show that compounds I induces a clear increase in the percentage of cells over-expressing ROS in a concentration dependent manner. In contrast compounds III, V, VIII and X were unable to induce ROS accumulation significantly in the treated cells. The expression of ROS correlated with the disruption of mitochondrial membrane potential as show in FIG. 9B.

Example 10

Comparative Reaction of VCE-004 and Compound XI with Cysteamine

Ten mg of VCE-004 (compound I) and compound XI (as example of the CBD-derivatives of the invention, applicable to the other members of the compound family of aforesaid derivatives II to X and XII to XV) were independently dissolved in 1 mL DMSO, and the solution was treated with an excess (4 mol. equivalents) of cysteamine. After stirring at room temperature for 1 h, the solutions were diluted with water (2 mL) and extracted with petroleum ether-ether 9:1. After evaporation, the residues were dissolved in $CDCl_3$ analyzed by $^1$H-NMR. While compound XI was recovered unscathed, VCE-004 (I) had completely reacted, and was undetectable in the residues indicating that VCE-004 was irreversibly bound to cysteamine.

The present results substantiate the therapeutic use of the compounds described in the present invention, particularly compounds III, V, VIII, X and XIII in neurodegenerative diseases and traumatic brain disorders where neuroinflammation and neurotoxicity play a significant role. In addition the compounds of the invention are particularly suitable as PPARg modulator particularly for treating diseases and conditions responsive to PPARg modulation.

REFERENCES

Ahmadian M, Suh J M, Hah N, Liddle C, Atkins A R, Downes M, Evans R M. 2013. PPARγ signaling and metabolism: the good, the bad and the future. Nat Med. 19:557-66

Barish G D, Narkar V A, Evans R M. 2006. PPARδ: a dagger in the heart of the metabolic syndrome. J Clin Invest. 116:590-597

Bernardo A, Minghetti L. 2008. Regulation of Glial Cell Functions by PPAR-gamma natural and Synthetic Agonists. PPAR Res. 864140.

Bolton J L, Trush M A, Penning T M, Dryhurst G, Monks T J. 2000. Role of quinones in toxicology. Chem Res Toxicol. 3:135-60.

Burstein S. 2005. PPAR-gamma: a nuclear receptor with affinity for cannabinoids. Life Sci. 77:1674-84.

Ciudin A, Hernandez C, Simó R. 2012. Update on cardiovascular safety of PPARgamma agonists and relevance to medicinal chemistry and clinical pharmacology. Curr Top Med Chem. 12: 585-604.

Doshi L S, Brahma M K, Bahirat U A, Dixit A V, Nemmani K V. 2012. Discovery and development of selective PPAR gamma modulators as safe and effective antidiabetic agents. Expert Opin Investig Drugs. 19:489-512.

Ferguson H E, Kulkarni A, Lehmann G M, Garcia-Bates T M, Thatcher T H, Huxlin K R. et al. 2009. Electrophilic peroxisome proliferator-activated receptor-gamma ligands have potent antifibrotic effects in human lung fibroblasts. Am J Respir Cell Mol Biol. 41:722-30.

Fievet C, Fruchart J C, Staels B. 2006. PPAR alpha and PPAR gamma dual agonists for the treatment of type2 diabetes and the metabolicsyndrome. Curr. Opin. Pharmacol. 6: 606-614.

Gelman, L., Feige, J. N., Desvergne, B. 2007. Molecular basis of selective PPARgamma modulation for the treatment of type 2 diabetes. Biochim. Biophys. Acta 1771: 1094-1107.

Ghoochani A, Shabani K, Peymani M, Ghaedi K, Karamali F, Karbalaei K, Tanhaie S, Salamian A, Esmaeili A, Valian-Borujeni S, Hashemi M, Nasr-Esfahani M H, Baharvand H. 2012. The influence of peroxisome proliferator-activated receptor g(1) during differentiation of mouse embryonic stem cells to neural cells. Differentiation. 83: 60-67

Granja A G, Carrillo-Salinas F, Pagani A, Gómez-Cañas M, Negri R, Navarrete C, Mecha M, Mestre L, Fiebich B L, Cantarero I, Calzado M A, Bellido M L, Fernandez-Ruiz J, Appendino G, Guaza C, Muñoz E. 2012. A cannabigerol quinone alleviates neuroinflammation in a chronic model of multiple sclerosis. J Neuroimmune Pharmaco1.4:1002-1016

Itoh T, Fairall L, Amin K, Inaba Y, Szanto A, Balint B L, Nagy L, Yamamoto K, Schwabe J W. 2008. Structural basis for the activation of PPARgamma by oxidized fatty acids. Nat Struct Mol Biol 15:924-931.

Kogan N M, Rabinowitz R, Levi P, Gibson D, Sandor P, Schlesinger M, and Mechoulam R. 2004. Synthesis and antitumor activity of quinonoid derivatives of cannabinoids. J Med Chem 47: 3800-3806

Lehmann J M, Moore L B, Smith-Oliver T A, Wilkison W O, Willson T M, Kliewer S A. 1995. An antidiabetic thiazolidinedione is a high affinity ligand for peroxisome proliferator-activated receptor gamma (PPAR gamma). J Biol Chem. 270:12953-12956.

Li Y, Zhang J, Schopfer F J, Martynowski D, Garcia-Barrio M T, Kovach A, Suino-Powell K, Baker P R, Freeman B A, Chen Y E, Xu H E. 2008. Molecular recognition of nitrated fatty acids by PPAR gamma. Nat Struct Mol Biol 15: 865-867

Liberato M V, Nascimento A S, Ayers S D, Lin J Z, Cvoro A, Silveira R L, Martinez L, Souza P C, Saidemberg D, Deng T, Amato A A, Togashi M, Hsueh W A, Phillips K, Palma M S, Neves F A, Skaf M S, Webb P, Polikarpov I. 2012. Medium Chain Fatty Acids Are Selective Peroxisome Proliferator activated Receptor (PPAR) c Activators and Pan-PPAR Partial Agonists. Plos One 7 e36297.

Liu J, Li H, Burstein S H, Zurier R B, Chen J D. 2003. Activation and binding of peroxisome proliferator-activated receptor gamma by synthetic cannabinoid ajulemic acid. Mol. Pharmacol. 63: 983-992.

Monks T J, Jones D C. 2002. The metabolism and toxicity of quinones, quinonimines, quinone methides, and quinone-thioethers. Curr Drug Metab. 4:425-38.

Morales P, Vara D, Goméz-Cañas M, Zfuliga M C, Olea-Azar C, Goya P, Fernández-Ruiz J, Diaz-Laviada I, Jagerovic N. 2013. Synthetic cannabinoid quinones: preparation, in vitro antiproliferative effects and in vivo prostate antitumor activity. Eur J Med Chem. 70: 111-119.

Na H K, Surh Y J. 2013. Oncogenic potential of Nrf2 and its principal target protein heme oxygenase-1. Free Radic Biol Med. 67:353-365

Nolte R T, Wisely G B, Westin S, Cobb J E, Lambert M H, Kurokawa R, Rosenfeld M G, Willson T M, Glass C K, Milburn M V. 1998. Ligand binding and co-activator assembly of the peroxisome pro liferator-activated receptor-gamma. Nature 395: 137-143.

O'Sullivan S E. 2007. Cannabinoids go nuclear: evidence for activation of peroxisome proliferator-activated receptors. Br J Pharmaco1.152:576-82.

Poulsen L, Siersbaek M, Mandrup S. PPARs: fatty acid sensors controlling metabolism. 2012. Semin Cell Dev Biol. 23:631-639.

Rosen E D, MacDougald O A. 2006. Adipocyte differentiation from the inside out. Nat Rev Mol Cell Biol. 7:885-96.

Solis L M, Behrens C, Dong W, Suraokar M, Ozburn N C, Moran C A, Corvalan A H, Biswal S, Swisher S G, Bekele B N, Minna J D, Stewart D J, Wistuba I I. 2010. Nrf2 and Keap1 abnormalities in non-small cell lung carcinoma and association with clinicopathologic features. Clin Cancer Res. 16:3743-53

M. B. Sporn, K. T. Liby. 2012. NRF2 and cancer: the good, the bad and the importance of context. Nat. Rev. Cancer. 12: 564-57 Stienstra R, Duval C, Muller M, Kersten S, 2007. PPARs, obesity, and inflammation. PPAR Res. 95974.

Sun Y, Bennett A. 2007. Cannabinoids: A New Group of Agonists of PPARs. PPAR Res. 23513.

Széles, L., Töröcsik, D., Nagy, L., 2007. PPARgamma in immunity and inflammation: cell types and diseases. Biochim. Biophys. Acta 1771: 1014-1030.

Tachibana K, Yamasaki D, Ishimoto K, Doi T. 2008. The Role of PPARs in Cancer. PPAR Res. 102737.

Tontonoz P, Spiegelman B M. 2008. Fat and beyond: the diverse biology of PPARgamma. Annu Rev Biochem. 77: 289-312.

Vanden Berghe W, Vermeulen L, Delerive P, DeBosscher K Staels B, Haegeman G. 2003. A paradigm for gene regulation: inflammation, N F-kB and PPAR. Adv. Exp. Med. Biol. 544:181-196.

Vivacell Biotechnology Esparia, S. L. 2011. Cannabinoid quinone derivatives. W O 2011117429 A1.

Wang W, Liu F, Chen N. 2007. Peroxisome proliferator-activated receptor-gamma (PPAR-gamma) agonists attenuate the profibrotic response induced by TGF-beta1 in renal interstitial fibroblasts. Mediators Inflamm: 62641

Zhao C, Chen W, Yang L, Chen L, Stimpson S A, Diehl A M. 2006. PPARgamma agonists prevent TGFbeta1/Smad3-signaling in human hepatic stellate cells. Biochem Biophys Res Commun 350: 385-391.

Zhang G Y, Yi C G, Li X, Ma B, Li Z J, Chen X L. Guo S Z, Gao W Y. 2009. Troglitazone suppresses transforming growth factor-beta1-induced collagen type I expression in keloid fibroblasts. Br J Dermatol. 160:762-70

What is claimed is:

1. Compounds of Formula (I), or pharmaceutically acceptable salts thereof

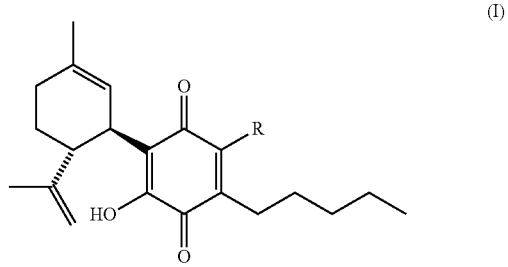

(I)

wherein R is the carbon atom of a linear or branched group, represented by alkoxycarbonyl groups; or wherein R is the nitrogen atom of a linear or branched group represented by: alkylamine, arylamine, alkenylamine or alkynylamine groups.

2. Compound according to claim 1 selected from:

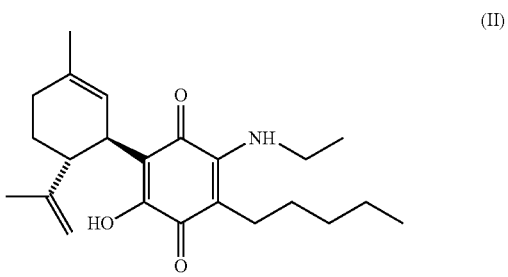

(II)

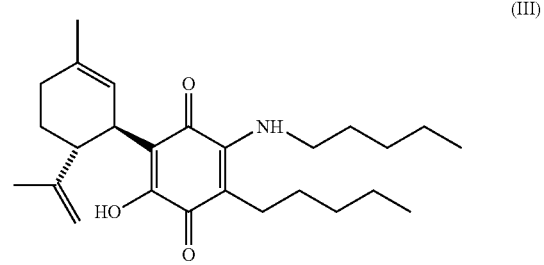

(III)

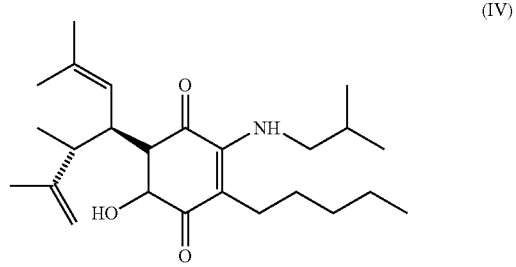

(IV)

(V) 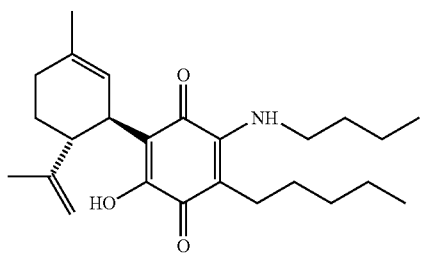
(VI) 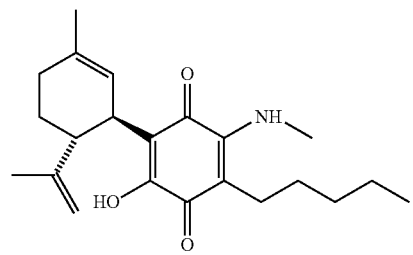
(VII) 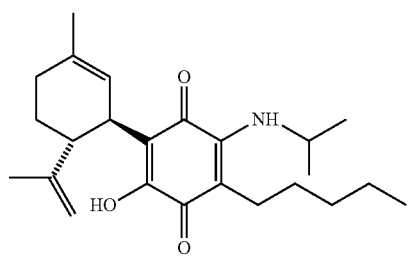
(VIII) 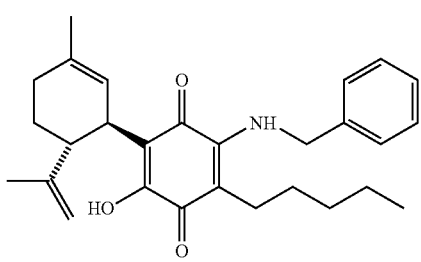
(IX) 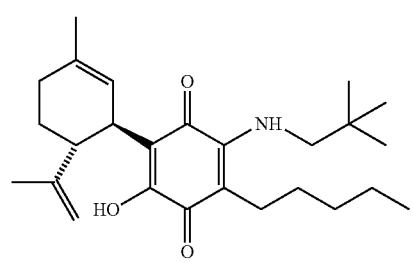
(X) 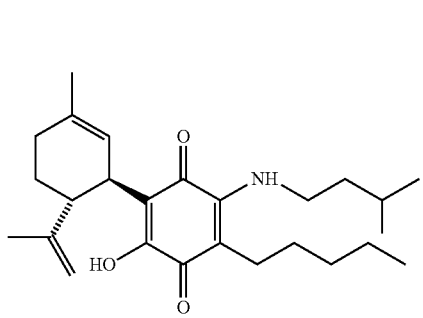
(XI) 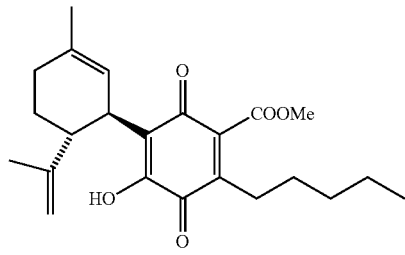
(XII) 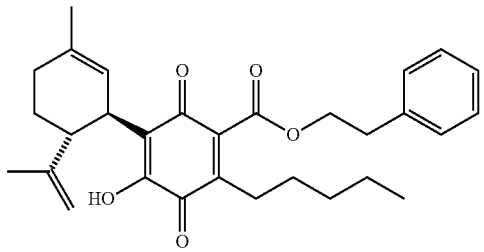
(XIII) 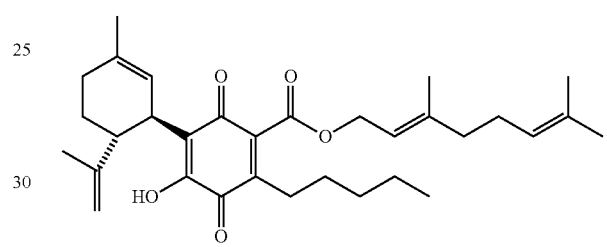
(XIV) 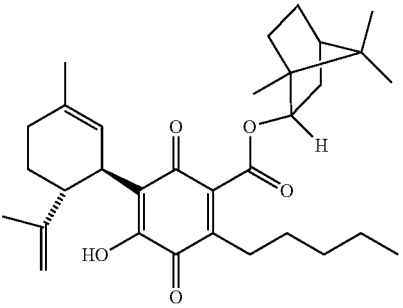
(XV) 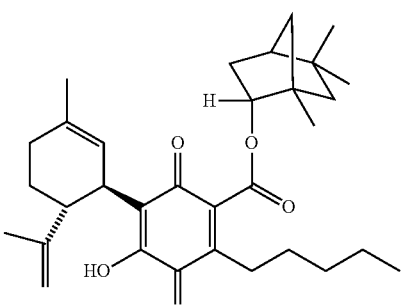
3. Compositions comprising a compound of claim 1, further comprising at least a pharmaceutical inert ingredient selected from an excipient or carrier.
4. Composition according to claim 3 wherein the compound of formula (I) is selected from:

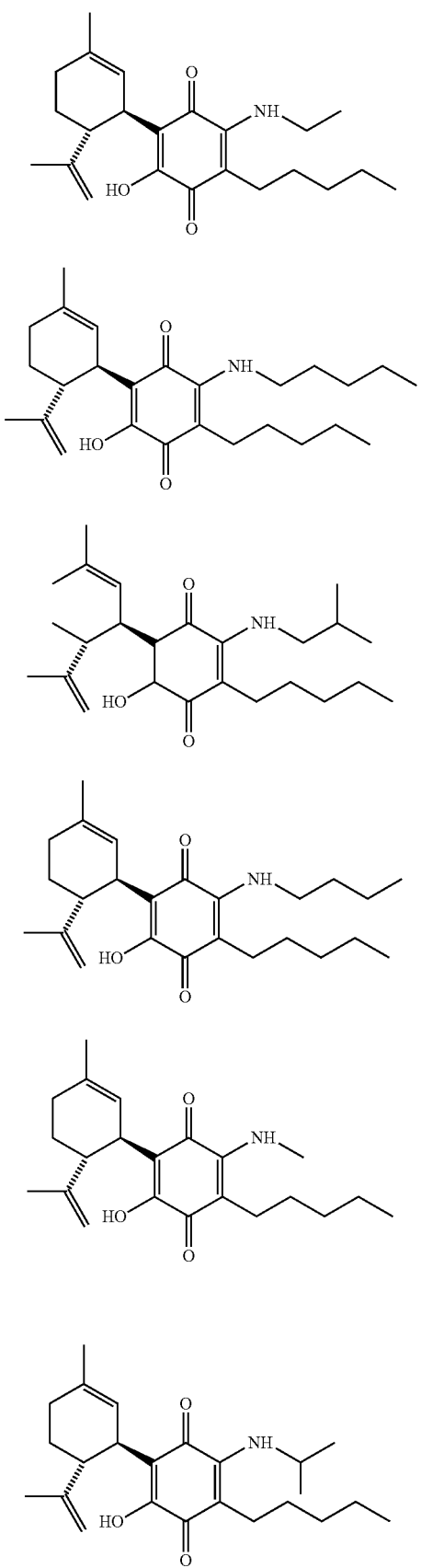
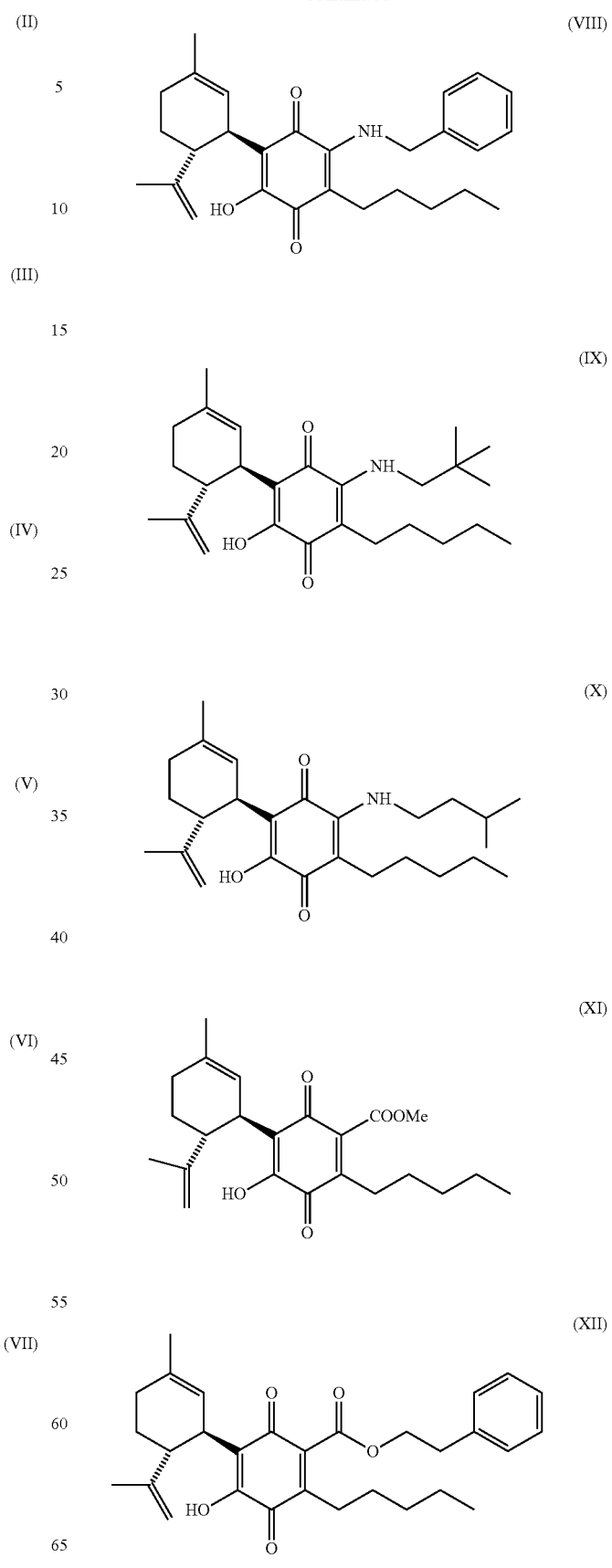

(XIII)

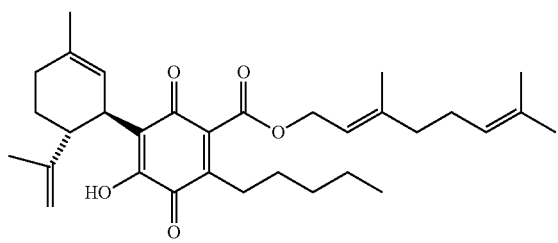

(XV)

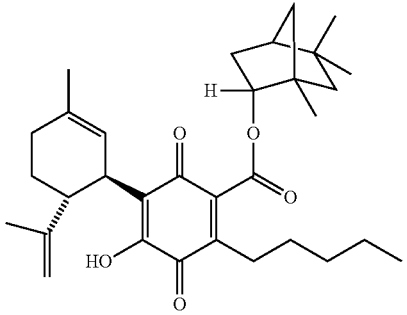

(XIV)

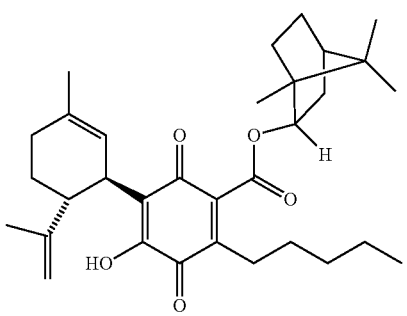

5. A medicament comprising a compound of claim 1.

6. A method of treating a human or animal patient comprising administering an effective amount of a medicament comprising the compound of claim 1 or a pharmaceutically acceptable salt thereof to the patient sufficient to ameliorate the symptoms of a disease, wherein the disease is a PPARg mediated disease.

7. The method of claim 6, wherein the PPARg mediated disease is selected from: atherosclerosis, inflammatory bowel diseases, rheumatoid arthritis, liver fibrosis, nephropathy, psoriasis, skin wound healing, skin regeneration, pancreatitis, gastritis, neurodegenerative disorders, neuroinflammatory disorders, scleroderma, cancer, hypertension, obesity, or type II diabetes.

* * * * *